US012738349B2

(12) United States Patent
Sauer

(10) Patent No.: US 12,738,349 B2
(45) Date of Patent: Sep. 15, 2026

(54) MACHINE LEARNING PEER REVIEW SYSTEM

(71) Applicant: MedAxiom Platforms Inc., Neptune Beach, FL (US)

(72) Inventor: Joel R. Sauer, Fort Wayne, IN (US)

(73) Assignee: MedAxiom Platforms Inc., Neptune Beach, FL (US)

( * ) Notice: Subject to any disclaimer, the term of this patent is extended or adjusted under 35 U.S.C. 154(b) by 202 days.

(21) Appl. No.: 18/355,007

(22) Filed: Jul. 19, 2023

(65) Prior Publication Data

US 2025/0029691 A1 Jan. 23, 2025

(51) Int. Cl.

| | |
|---|---|
| ***G16H 20/70*** | (2018.01) |
| ***G06N 3/084*** | (2023.01) |
| ***G16H 10/60*** | (2018.01) |
| ***G16H 15/00*** | (2018.01) |
| ***G16H 40/67*** | (2018.01) |
| ***G16H 50/30*** | (2018.01) |

(52) U.S. Cl.
CPC ............. *G16H 10/60* (2018.01); *G06N 3/084* (2013.01); *G16H 15/00* (2018.01)

(58) Field of Classification Search
CPC ........ G16H 10/60; G16H 15/00; G16H 20/00; G16H 40/20; G06N 3/084
See application file for complete search history.

(56) References Cited

U.S. PATENT DOCUMENTS

| | | | | |
|---|---|---|---|---|
| 2017/0372029 | A1* | 12/2017 | Saliman | G16H 10/60 |
| 2020/0342969 | A1* | 10/2020 | White | G06Q 30/0206 |
| 2022/0036281 | A1* | 2/2022 | Chekroud | G16H 40/20 |
| 2023/0154612 | A1* | 5/2023 | Sargent | G16H 30/40 705/3 |
| 2024/0387020 | A1* | 11/2024 | Glick | G16H 40/20 |

* cited by examiner

*Primary Examiner* — Maroun P Kanaan
(74) *Attorney, Agent, or Firm* — Jeffri A. Kaminski; Venable LLP

(57) ABSTRACT

A system for peer review includes a storage configured to receive a request from a medical provider. The request includes identified medical data that is uniquely associated with a patient and the medical provider. The system further includes an anonymizer, configured to receive identified medical data from the storage, generate anonymized medical data by normalizing the identified medical data to remove any association with the patient and the medical provider, and provide the resulting anonymized medical data to a plurality of reviewers. The system further includes a score generator configured to receive assessments from the reviewers of the anonymized medical data, and generate a score based on the assessments, representing a quality of a treatment of the patient by the medical provider. The system further includes a report generator, configured to receive the score from the score generator, and provide a report with the score to the medical provider.

24 Claims, 9 Drawing Sheets

MACHINE LEARNING PEER REVIEW SYSTEM

BACKGROUND

1. Technical Field

Currently claimed embodiments of the invention relate to systems for computerized peer review, and more specifically, machine learning systems for peer review of medical treatments.

2. Discussion of Related Art

The health care system in the United States suffers up to a trillion dollars in wasted care costs annually. According to some studies, overtreatment and low-value care may account for $75 billion to $101 billion of these wasted dollars. Peer review provides a mechanism to improve the quality of care, but a number of obstacles serve as a disincentive for treatment providers from engaging in peer review and accepting peer recommendations. These obstacles include the lack of a safe environment for feedback, and providers' concerns about competition, politics, reputation, and identity. A peer review system that solves these problems, as well as protects patient data from disclosure, and facilitates "best practice" dissemination, would improve patient care and safety as well as reduce the cost of health care overall.

SUMMARY

According to an embodiment of the invention, a method for peer review includes receiving a request from a medical provider, the request including identified medical data that is uniquely associated with a patient and that is uniquely associated with the medical provider; generating anonymized medical data by normalizing the identified medical data to remove any association with the patient and to remove any association with the medical provider, resulting in anonymized medical data; providing the anonymized medical data to multiple reviewers; receiving, from the reviewers, multiple assessments of the anonymized medical data; generating a score based on the assessments; and providing a report including the score to the medical provider, the score representing a quality of a treatment of the patient by the medical provider.

According to an embodiment of the invention, a system for peer review includes a processor and a storage that is configured to receive a request from a medical provider, the request including identified medical data that is uniquely associated with a patient and that is uniquely associated with the medical provider. The system further includes an anonymizer, configured to receive the identified medical data from the storage, generate anonymized medical data by normalizing the identified medical data to remove any association with the patient and to remove any association with the medical provider, resulting in anonymized medical data, and provide the anonymized medical data to multiple reviewers. The system further includes a score generator, configured to receive, from the reviewers, multiple assessments of the anonymized medical data, and generate a score based on the assessments, the score representing a quality of a treatment of the patient by the medical provider. The system further includes a report generator, configured to receive the score from the score generator, and provide a report including the score to the medical provider. The system further includes a non-transitory computer readable medium storing a set of instructions, which when executed by the processor, configure the anonymizer, the score generator, and the report generator.

According to an embodiment of the invention, a non-transitory computer-readable medium stores a set of instructions for peer review, which when executed by a computer, configure the computer to receive a request from a medical provider, the request including identified medical data that is uniquely associated with a patient and that is uniquely associated with the medical provider; generate anonymized medical data by normalizing the identified medical data to remove any association with the patient and to remove any association with the medical provider, resulting in anonymized medical data; provide the anonymized medical data to multiple reviewers; receive, from the reviewers, multiple assessments of the anonymized medical data; generate a score based on the assessments; and provide a report including the score to the medical provider, the score representing a quality of a treatment of the patient by the medical provider.

BRIEF DESCRIPTION OF THE DRAWINGS

Further objectives and advantages will become apparent from a consideration of the description, drawings, and examples.

DETAILED DESCRIPTION

Figure 1:
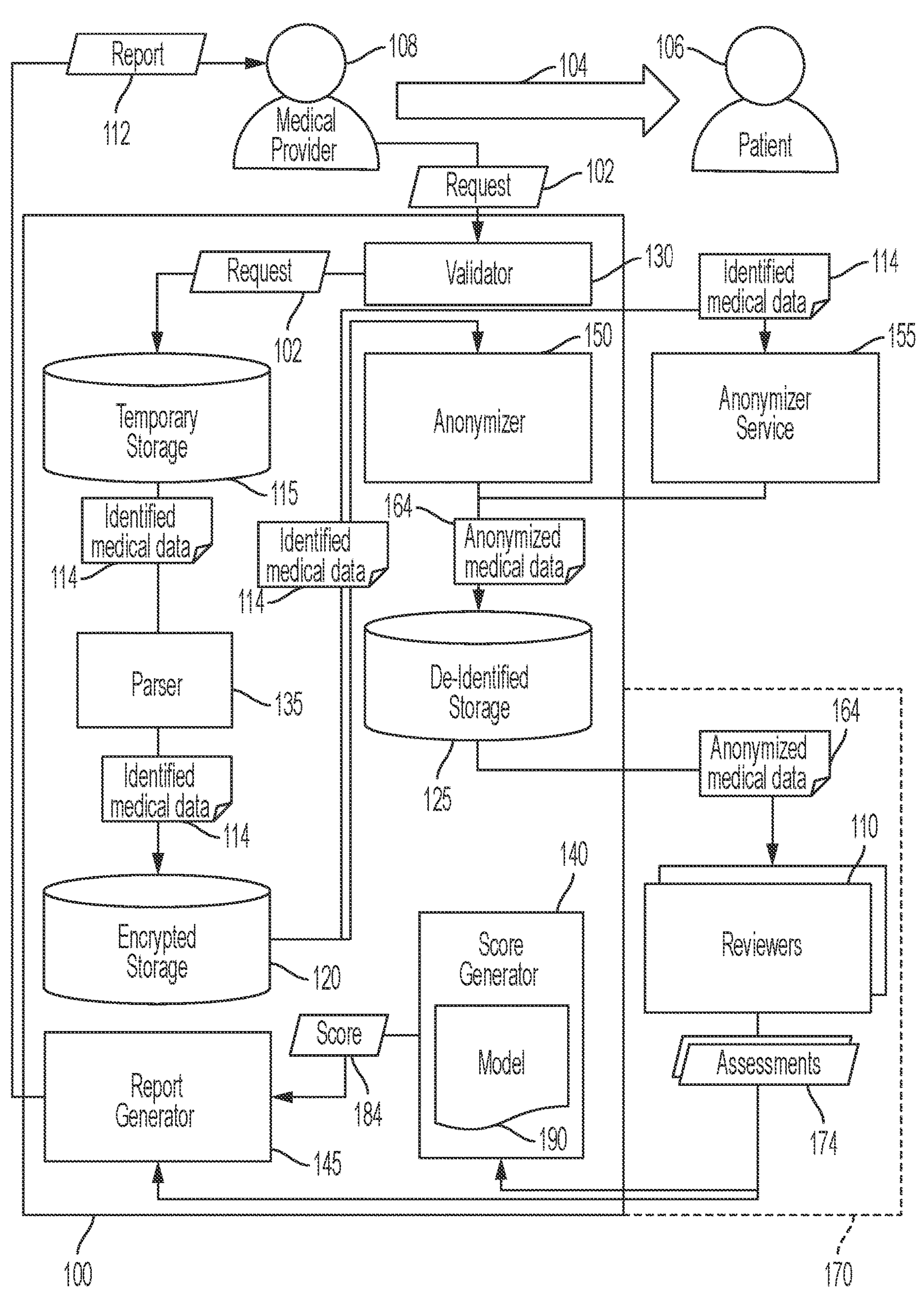
FIG. 1 shows a system for peer review, according to some embodiments.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed, and other methods developed, without departing from the broad concepts of the current invention.

The term "medical organization" as used herein refers to a group or entity that provides medical services, facilities, or resources to patients or medical providers. Examples of medical organizations include, but are not limited to, hospitals, clinics, medical practices, research institutions, corporations, and other entities involved in the development, delivery, or management of medical care.

The term "medical provider" as used herein refers to a person that is capable (e.g., legally, professionally, etc.) of providing a treatment to a patient. Examples of medical providers include, but are not limited to, physicians, nurses, pharmacists, dentists, and other types of licensed health professionals and health practitioners. A medical provider may have a relationship with a medical organization, including but not limited to being an employee, being an owner, being a resident or a student, being a partner, or having attending privileges therewith.

The term "treatment" as used herein refers to any method or procedure that aims to diagnose, prevent, cure, or alleviate a medical condition (e.g., a disease, a chronic illness, an acute illness, etc.) in a patient. Treatments may include, but are not limited to, one or more of administration of drugs, surgical procedures, physical therapy, and other medical interventions, including diagnostic procedures and management of medical conditions. The goal of the treatment is to improve the health or well-being of the patient, by directly or indirectly addressing the underlying cause of the medical condition and managing its symptoms.

The term "medical data" as used herein refers to a patient's medical health record, which includes but is not limited to medical diagnoses, treatment plans and treatment history, medication records, lab results, imaging results, family history, genetic information, and disease history.

The term "identified medical data" as used herein refers to medical data that contains private health information (PHI) of a patient, and therefore can be used to link the patient's PHI to the patient's identity. Examples of PHI include, but are not limited to, the patient's name, address, date of birth (DOB), contact information (e.g., phone number, email address, social media accounts, etc.), social security number (SSN), insurance information, and other personal identifiers.

The term "anonymized medical data" as used herein refers to medical data that was previously identified medical data containing PHI, but which has been processed to remove all PHI. Anonymized medical data cannot be used to identify the patient and preserves the patient's privacy, in compliance with privacy laws such as the federal Health Insurance Portability and Accountability Act (HIPAA) and similar state-level statutes in the United States. Processing medical data to remove PHI may be equivalently referred to as "normalizing," "de-identifying," or "anonymizing" the data.

The term "encrypted" medical data refers to medical data (either identified or anonymized) that has been secured using at least one mathematical "key" so that only an authorizer user may access the data. For example, in some embodiments, encryption may utilize an asymmetric encryption technique that relies on the use of two keys, one public and one private, to encrypt the medical data. In other embodiments, encryption may utilize a symmetric encryption technique which uses a single private key to encrypt the medical data. Accessing the encrypted data likewise requires using at least one "key" to decrypt the encrypted medical data (which may or may not be the same key used to encrypt the data).

The term "reviewer" as used herein refers to a medical provider who reviews the medical decisions made by another medical provider, and provides feedback on whether those decisions (e.g., diagnosis, treatment, etc.) are in line with accepted medical practice and the reviewer's own experience and judgement. Accepted medical practice may be defined by a number of authoritative sources, including but not limited to medical organizations, medical societies, and clinical studies.

The term "service" as used herein refers to a process that receives data from a source as input, performs at least one operation on said data to generate an output, and provides said output to the source. In some embodiments, a service may be an internal process, including but not limited to a software application. In other embodiments, a service may be an external process, including but not limited to an application programming interface (API).

Some embodiments provide a platform for anonymized peer review, by multiple peer reviewers, of the medical treatment of a patient by a medical provider. The peer review platform is external to the medical provider, and conducted by peer reviewers who are not aware of the identity of the medical provider, and whose identities are unknown to the medical provider. The peer reviewers are randomly chosen in some embodiments, from a pool of experts in the field of the medical treatment that spans multiple geographic locations and multiple institutional organizations. The platform normalizes and anonymizes the patient health information pertaining to the medical treatment. The medical information pertaining to the patient treatment is anonymized and protected so that the platform itself never has access to private patient health information.

In some embodiments, the reviews are conducted within the platform by the reviewers so that anonymized patient health information is never exposed outside the platform. The reviews from each of the reviewers are aggregated and may be presented to the medical provider as a score, a report, or combination thereof to indicate the quality of the medical treatment according to medical consensus and optimal medical practice. In some embodiments, the report, score, etc. are presented to the medical provider within the same platform used for review by the peer reviewers.

FIG. 1 shows a computer system 100 for peer review, according to some embodiments. The system 100 receives and processes various electronic messages and database records. For example, the system 100 receives a request 102 for peer review of a treatment 104 of a patient 106 from a medical provider 108, provides details of the treatment 104 to a set of reviewers 110 for review, and provides a report 112 back to the medical provider 108 on the quality of the treatment 104, as assessed by the reviewers 110. The report 112 is an anonymized report that does not identify any of the reviewers 110.

In some embodiments, the request 102 includes identified medical data 114 that is uniquely associated with the patient 106 and the medical provider 108. The request 102 is encrypted to ensure that the identified medical data 114 remains private within the system 100. The technique used to encrypt the request 102 may include, but is not limited to, shared secret techniques, symmetric encryption techniques, and asymmetric encryption techniques. In some embodiments, the encryption technique may use encryption metadata (e.g., a shared secret, a public key, a private key, etc.).

The identified medical data 114 also includes a description of the treatment 104. The description of the treatment 104 may include, for example, a description of a medical condition of the patient 106, the treatment 104 being for the medical condition. The identified medical data 114 may also include one or more of a date (e.g., the date of the treatment 104), a case number, and an account identifier.

The system 100 includes a processor (not shown), a temporary storage 115, an encrypted storage 120 for identified medical data, and a de-identified storage 125 for de-identified (e.g., anonymized) medical data. The system 100 also includes a validator 130, an parser 135, a score generator 140, and a report generator 145. The system 100 may include an anonymizer 150, be in communication with an external anonymizer service 155, or both. The system 100 may also include a non-transitory computer readable medium (not shown), that stores a set of instructions, which when executed by the processor, configure one or more of the validator 130, the parser 135, the score generator 140, the report generator 145, and the anonymizer 150 to perform the operations described below.

The request 102 is received by the system 100 from the medical provider 108 and stored in the temporary storage 115. The temporary storage 115 is a reserved area for temporary storage of encrypted data, such as a directory or other specified area on disk. The temporary storage 115 may be periodically flushed of all data stored therein, and/or may selectively remove data after a specified period of time.

In some embodiments, the validator 130 receives the request 102 from the medical provider 108 and validates the request 102 to determine whether the identified medical data 114 therein is complete. If the validator 130 determines that the identified medical data 114 is complete, the validator 130 stores the request 102 (including the identified medical data 114) in the temporary storage 115.

In some embodiments, the validator 130 validates the request 102 by determining that the request 102 includes information that is relevant to the treatment 104. Relevant information may vary depending on the type of medical condition and treatment 104. As an example, Table 1 provides a peer review framework with examples of relevant information. The validator 130 may be configured to check for any or all of the information in Table 1.

TABLE 1

| | | |
|---|---|---|
| Clinical decision leading to the intervention | Most recent clinical notes - pre & post intervention | Most recent office note (with med reconciliation)<br>Prior cath/intervention report including hemodynamics<br>Discharge summary |
| | Imaging | Echo reports and studies - TTE/TEE<br>CT/MR reports<br>Cath/interventional images<br>IVUS images |
| | Diagnostic testing (labs, EKGs, etc.) | Labs<br>EKGs |
| | Procedure imaging (in addition to above) | Cath lab studies: diagnostic and intervention - in addition to the case in review include any previous studies/interventions within the last 2-3 years |
| | Clinical notes/reports (in addition to above) | All available consults during encounter<br>Heart Team recommendations (if available) |
| Technical details of the case, including film | Clinical notes (in addition to the above) | Procedure report from hemodynamics system<br>Pre- and post-procedure care notes and vital signs<br>Medication administration record pre/post procedure<br>Any other notes associated with the procedure (anesthesia, respiratory therapy, etc.) |
| Objective data | Any intra-procedure data not included in the hemodynamic system report | FFR, OCT, IABP, Impella, etc.<br>AUC documentation |

In some embodiments, the parser 135 retrieves the identified medical data 114 from the temporary storage 115 and performs an extract-load-transform (ETL) operation to store the identified medical data 114 in the encrypted storage 120. The encrypted storage 120 is an encrypted database in some embodiments, and the identified medical data 114 is formatted by the parser 135 and stored in the encrypted storage 120 as an encrypted database record. The parser 135 may then delete the identified medical data 114 from the temporary storage 115.

In some embodiments, the anonymizer 150 retrieves the identified medical data 114 from the encrypted storage 120. The anonymizer 150 generates anonymized medical data 164 by normalizing the identified medical data 114 to remove any association with the patient 106 and the medical provider 108, resulting in the anonymized medical data 164.

In some embodiments, the system 100 provides the identified medical data 114 to the anonymizer service 155. The anonymizer service 155 generates the anonymized medical data 164 by normalizing the identified medical data 114 to remove any association with the patient 106 and the medical provider 108, resulting in the anonymized medical data 164. The anonymizer service 155 may be, but is not limited to, an application programming interface (API).

The anonymized medical data 164 is stored (e.g., by the anonymizer 150, or the anonymizer service 155) in the de-identified storage 125. The system 100 provides the anonymized medical data 164 from the de-identified storage 125 to the reviewers 110.

In some embodiments, prior to providing the anonymized medical data 164 to the reviewers 110, the validator 130 retrieves the anonymized medical data 164 from the de-identified storage 125 and validates the anonymized medical data 164 to determine whether the anonymized medical data 164 is complete. If the validator 130 determines that the anonymized medical data 164 is complete, the system 100 (e.g., the validator 130) provides the anonymized medical data 164 to the reviewers 110. This validation in some embodiments of the anonymized medical data 164 is not shown in FIG. 1.

In some embodiments, the reviewers 110 access the anonymized medical data 164 through the system 100, so that the anonymized medical data 164 does not leave the system 100. For example, the anonymized medical data 164 may be accessed, in read-only fashion, via a graphical user interface 170 (shown in FIG. 1 as a dashed line) directly from the de-identified storage 125.

After assessing the anonymized medical data 164 and performing a review of the treatment 104 of the patient 106, each of the reviewers 110 generate an assessment 174. The assessment 174 may be, for example, an assessment of the quality of the treatment 104 of the patient 106 by the medical provider 108. The assessments 174 may be different based on the different type of medical condition and the corresponding treatment 104. In some embodiments, the assessments 174 are generated within the graphical user interface 170. The assessments 174 from all the reviewers 110 are received by the score generator 140. In some embodiments, the assessments 174 from all the reviewers 110 are also received by the report generator 145.

The score generator 140 generates a score 184 based on the assessments 174. The score 184 represents a quality of the treatment 104 of the patient 106 by the medical provider 108. In some embodiments, the score generator 140 combines the assessments 174 into an aggregate assessment (not shown in FIG. 1) and generates the score 184 based on the aggregate assessment. In some embodiments, the score generator generates multiple initial scores (not shown in FIG. 1), each initial score corresponding to one of the assessments 174 by one of the reviewers 110. The score generator 140 combines the initial scores into the final score 184.

Table 2 illustrates an example of an assessment 174 used in some embodiments during a treatment 104 of a patient 106 having a heart condition. In this example the medical provider 108 may be a cardiologist, and the treatment 104 is a cardiac intervention, such as placement of a stent. The assessment 174 comprises a list of decisions, organized into categories, made by the medical provider 108. Each reviewer 110 ranks the decisions, e.g. on a scale of Optimal, Satisfactory, Unsatisfactory, and Not Applicable, or a binary scale of Yes or No.

The example of Table 2 also provides an example of aggregating individual reviewer assessments according to some embodiments. In this example, multiple assessments are shown, by different reviewers, for each decision. Each category also is assigned a weighting towards the total score, and the decisions in each category are assigned points. The assessments by each reviewer are scaled depending on their individual ratings and combined into a total score using the points for each decision and the category weighting. In this example, an optimal rating on a certain decision provides 100% of the points, a satisfactory rating provides 60% of the points, and an unsatisfactory rating provides 0% of the points. The total number of points are calculated across all reviewers for each decision, summed over all the decisions within a category, and weighted to calculate a final total score, represented as a percentage of the total possible points.

TABLE 2

| Category/Decision | Weight/ Points | Reviewer 1 Assessment | Reviewer 2 Assessment |
|---|---|---|---|
| PCI Decision Making | 20% | | |
| A thorough review was completed | 1 | Satisfactory | Satisfactory |
| Clinical indications support decision | 2 | Optimal | Optimal |
| Stress test results support decision | 2 | Satisfactory | Satisfactory |
| Imaging results support decision | 3 | Optimal | Optimal |
| Patient is appropriate for the procedure | 100 | Satisfactory | Satisfactory |
| Intra-Procedure | 70% | | |
| Clinical information supports access site | 2 | Satisfactory | Satisfactory |
| Documentation supports access site | 2 | Satisfactory | Satisfactory |
| Clinical information supports sheath size | 2 | Satisfactory | Satisfactory |
| Documentation supports sheath size | 2 | Satisfactory | Satisfactory |
| Ventriculography | 2 | Satisfactory | Satisfactory |
| Angiography quality | 2 | Satisfactory | Satisfactory |
| Was PCI for this lesion indicated | 100 | Unsatisfactory | Unsatisfactory |
| For all that apply please rank: | | | |
| Ultrasound Guided Vascular Access | 3 | Satisfactory | Satisfactory |
| Intracoronary Imaging | 4 | Unsatisfactory | Unsatisfactory |
| Intracoronary Physiologic Assessment | 4 | Satisfactory | Satisfactory |
| Pulmonary Artery Catheter | 3 | Satisfactory | Satisfactory |
| Mechanical Circulatory Support | 4 | Not Applicable | Not Applicable |
| PCI lesion was the culprit lesion | 4 | Unsatisfactory | Unsatisfactory |
| Stent Deployment | 100 | Satisfactory | Satisfactory |
| Closure device/technique used | 3 | Satisfactory | Satisfactory |
| Complications | 10% | | |
| Unexpected Mortality | 5 | No | No |
| Bleeding | 2 | Yes | Yes |
| AKI | 3 | No | No |

The report generator 145 receives the score 184 from the score generator 140 and includes the score in the report 112 that is provided to the medical provider 108. The report 112 may also include the assessments 174, or a portion thereof, or a summary thereof. In some embodiments, the report 112 further includes a comparison between the treatment 104 and an optimal treatment for the medical condition.

In some embodiments, the identified medical data 114 may be identified using a case number. In some such embodiments, the anonymizer 150 (or the anonymizer service 155) may generate the anonymized medical data 164 by removing all occurrences of the case number from the identified medical data 114. In some such embodiments, removing all occurrences of the case number includes replacing the case number with an anonymized case number, and associating the data with the anonymized case number in a database.

In some embodiments, the identified medical data 114 may be identified using an account identifier. In some such embodiments, the anonymizer 150 (or the anonymizer service 155) may generate the anonymized medical data 164 by removing all occurrences of the account identifier from the identified medical data 114. In some such embodiments, removing all occurrences of the account identifier includes replacing the account identifier with an anonymized account identifier, and associating the data with the anonymized account identifier in a database.

In some embodiments, the identified medical data 114 may be uniquely associated with the patient 106 by including a patient identifier. In some such embodiments, the anonymizer 150 (or the anonymizer service 155) may generate the anonymized medical data 164 by normalizing the identified medical data 114 to remove any association with the patient. For example, the association with the patient may be removed by removing all occurrences of the patient identifier from the identified medical data 114. In some such embodiments, removing all occurrences of the patient identifier includes replacing the patient identifier with an anonymized patient identifier, and associating the data with the anonymized patient identifier in a database.

In some embodiments, the identified medical data 114 may be uniquely associated with the medical provider 108 by including a provider identifier. In some such embodiments, the anonymizer 150 (or the anonymizer service 155) may generate the anonymized medical data 164 by normalizing the identified medical data 114 to remove any association with the medical provider. For example, the association with the medical provider may be removed by removing all occurrences of the provider identifier from the identified medical data 114. In some such embodiments, removing all occurrences of the provider identifier includes replacing the provider identifier with an anonymized provider identifier, and associating the data with the anonymized provider identifier in a database.

In some embodiments, the provider identifier may be or may include, for example, a National Provider Identifier (NPI) number, assigned by the Centers for Medicare and Medicaid Services (CMS).

In some embodiments, the identified medical data 114 may be uniquely associated with a medical organization (not shown in FIG. 1), e.g., by including an organization identifier. In some such embodiments, the anonymizer 150 (or the anonymizer service 155) may generate the anonymized medical data 164 by normalizing the identified medical data 114 to remove any association with the medical organization. For example, the association with the medical organization may be removed by removing all occurrences of the organization identifier from the identified medical data 114. In some such embodiments, removing all occurrences of the organization identifier includes replacing the organization identifier with an anonymized organization identifier, and associating the data with the anonymized organization identifier in a database.

In some embodiments, a threshold score is defined. A score 184 above the threshold score indicates that the quality of the treatment is a valid treatment, and a score 184 below the threshold score indicates the quality of the treatment is an invalid treatment. In some such embodiments, if the score 184 is below the threshold, indicating that the reviewers 110 generally found that the treatment 104 was not valid (e.g., relative to the optimal treatment for the medical condition), then the system 100 may provide the anonymized medical data 164 to additional reviewers 110. The assessments 174 from this second round of reviews may be used to update the score 184. This provides a second opinion on a treatment 104 that has been initially scored poorly, to ensure that a negative report 112 has credibility as a critique of the treatment 104. In some such embodiments, the score generator 140 generates additional initial scores from the second round of assessments 174 and combines the initial scores from the first and second rounds of assessments 174 to create a new score 184.

In some embodiments, the score generator 140 receives training data (not shown in FIG. 1), that includes descriptions of multiple previous treatments of multiple previous patients (not shown). The training data may further include multiple previous scores of the previous treatments. The training data may be used to train a model 190, resulting in a trained model 190 that is used by the score generator 140 to generate the score 184 from the assessments 174.

Figure 2A:
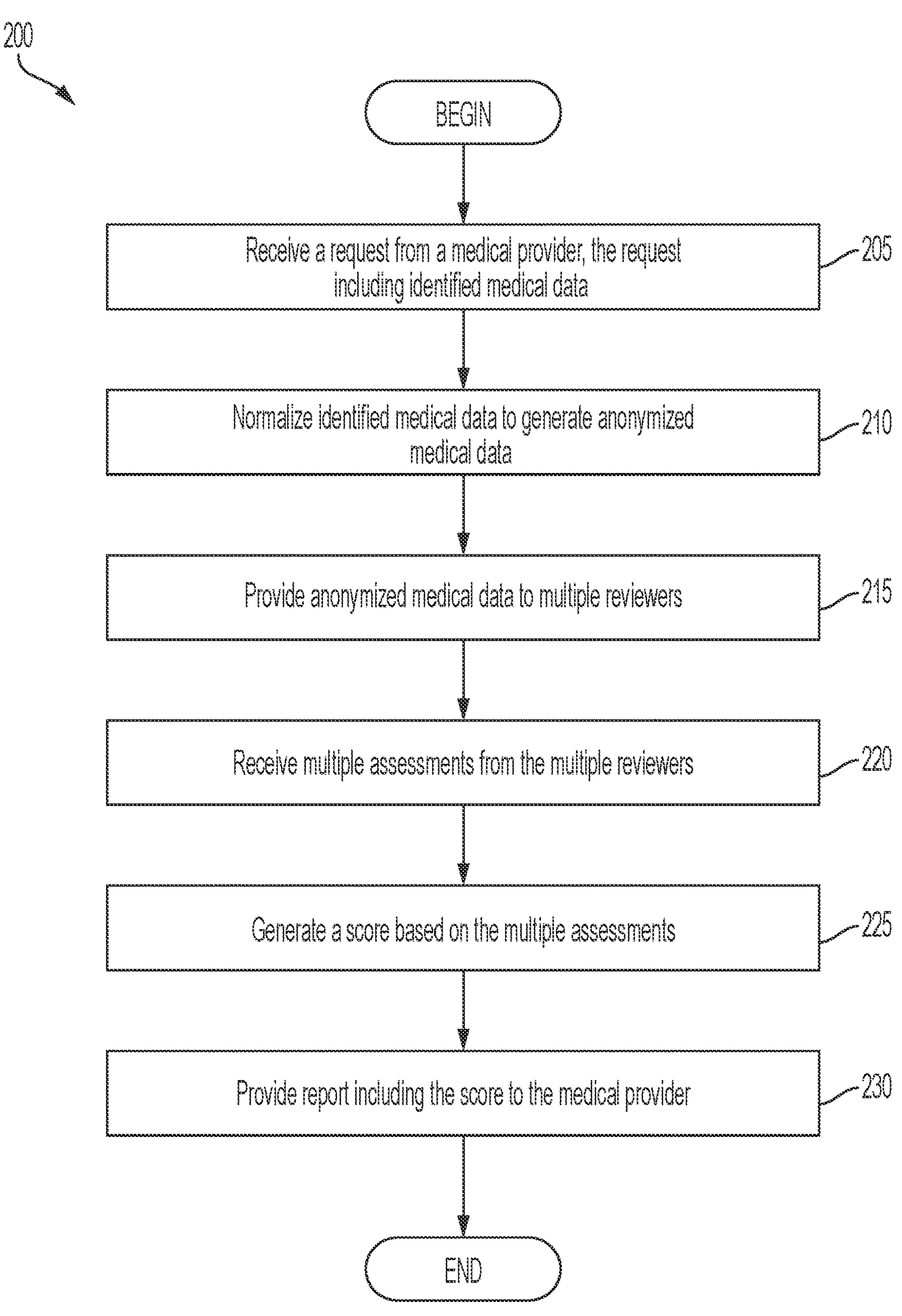
FIG. 2A shows a process performed by a system for peer review of some embodiments.

FIG. 2A shows a process 200 performed by a system for peer review of some embodiments. In some embodiments, the process 200 may be performed by the system 100 of FIG. 1, which is described above.

The process 200 begins at 205 by receiving a request (e.g., request 102) from a medical provider (e.g., medical provider 108) system. The request includes identified medical data (e.g., identified medical data 114) that in some embodiments is uniquely associated with the patient and the medical provider. In some embodiments, the request includes at least one of a date, a case number, and an account identifier.

At 210, the process 200 continues by normalizing the identified medical data to generate anonymized medical data (e.g., anonymized medical data 164). In some such embodiments, the identified medical data is normalized to remove any association with the patient and the medical provider. In some such embodiments, generating the anonymized medical data includes at least one of replacing the account identifier with an anonymized account identifier, and replacing the case number with an anonymized case number.

In some embodiments, the process 200 initially stores the identified medical data in a first storage (e.g., temporary storage 115, or encrypted storage 120) that is adapted for storing identified medical data. The process 200 stores the anonymized medical data a second storage (e.g., de-identified storage 125) adapted for storing anonymized (e.g., de-identified) medical data, and deletes the identified medical data from the first storage.

In some embodiments, the process 200 validates the request to determine whether the identified medical data is complete, prior to generating the anonymized medical data.

In some embodiments, the identified medical data is uniquely associated with the patient using a patient identifier and normalizing the identified medical data to remove any association with the patient includes removing all occurrences of the patient identifier from the identified medical data. In some such embodiments, removing all occurrences of the patient identifier includes replacing the patient identifier with an anonymized patient identifier.

In some embodiments, the identified medical data is uniquely associated with the medical provider using a provider identifier and normalizing the identified medical data to remove any association with the medical provider includes removing all occurrences of the provider identifier from the identified medical data. In some such embodiments, removing all occurrences of the provider identifier includes replacing the provider identifier with an anonymized provider identifier.

In some embodiments, the identified medical data is uniquely associated with a medical organization and generating the anonymized medical data includes further normalizing the identified medical data to remove any association with the medical organization. In some such embodiments, the identified medical data is uniquely associated with the medical organization using an organization identifier and normalizing the identified medical data to remove any association with the medical organization includes removing all occurrences of the organization identifier from the identified medical data. In some such embodiments, removing all occurrences of the organization identifier includes replacing the organization identifier with an anonymized organization identifier.

In some embodiments, the process 200 uses an anonymizer service (e.g., anonymizer service 155) to generate the anonymized medical data.

At 215, the process 200 continues by providing the anonymized medical data to a group of multiple reviewers (e.g., reviewers 110). In some embodiments, the process 200 validates the anonymized medical data to determine whether the anonymized medical data is complete, prior to providing the anonymized medical data to the reviewers. In some embodiments, the anonymized medical data is provided to the reviewers from the second storage.

In some embodiments, the reviewers 110 are a subset randomly selected from a larger pool of reviewers (not shown), where the selection may be filtered based on one or more criteria. The filtering criteria may include, but are not limited to, medical specialty and geographic location.

At 220, the process 200 continues by receiving from the reviewers, multiple assessments (e.g., assessments 174) of the anonymized medical data.

At 225, the process 200 continues by generating a score (e.g., score 184) based on the multiple assessments. In some embodiments, the score represents a quality of a treatment 104 of the patient by the medical provider.

In some embodiments, the process 200 generates the score based on the multiple assessments, by combining the assessments into a single aggregate assessment, and generating the score based on the aggregate assessment.

In some embodiments, the process 200 generates the score based on the multiple assessments, by generating multiple initial scores, each initial score corresponding to a single one of the assessments, and combining all the multiple initial scores into a final score (e.g., score 184).

In some embodiments, the identified medical data and the anonymized medical data include a description of the treatment (e.g., treatment 104), and the assessments include assessments of the quality of the treatment based on that description. In some such embodiments, the description of the treatment includes a description of a medical condition of the patient, the treatment being for the medical condition, and the report further includes a comparison between the treatment and reference treatment information for the medical condition. The reference treatment information may be, for example, an optimal treatment consensus defined by authoritative sources, including but not limited to other medical professionals, medical organizations, accreditation entities, and state and federal law.

At 230, the process 200 continues by providing a report (e.g., report 112), that includes the score, to the medical provider. The report may be an anonymized report that does not identify any of the reviewers. The process 200 then ends.

Figure 2B:
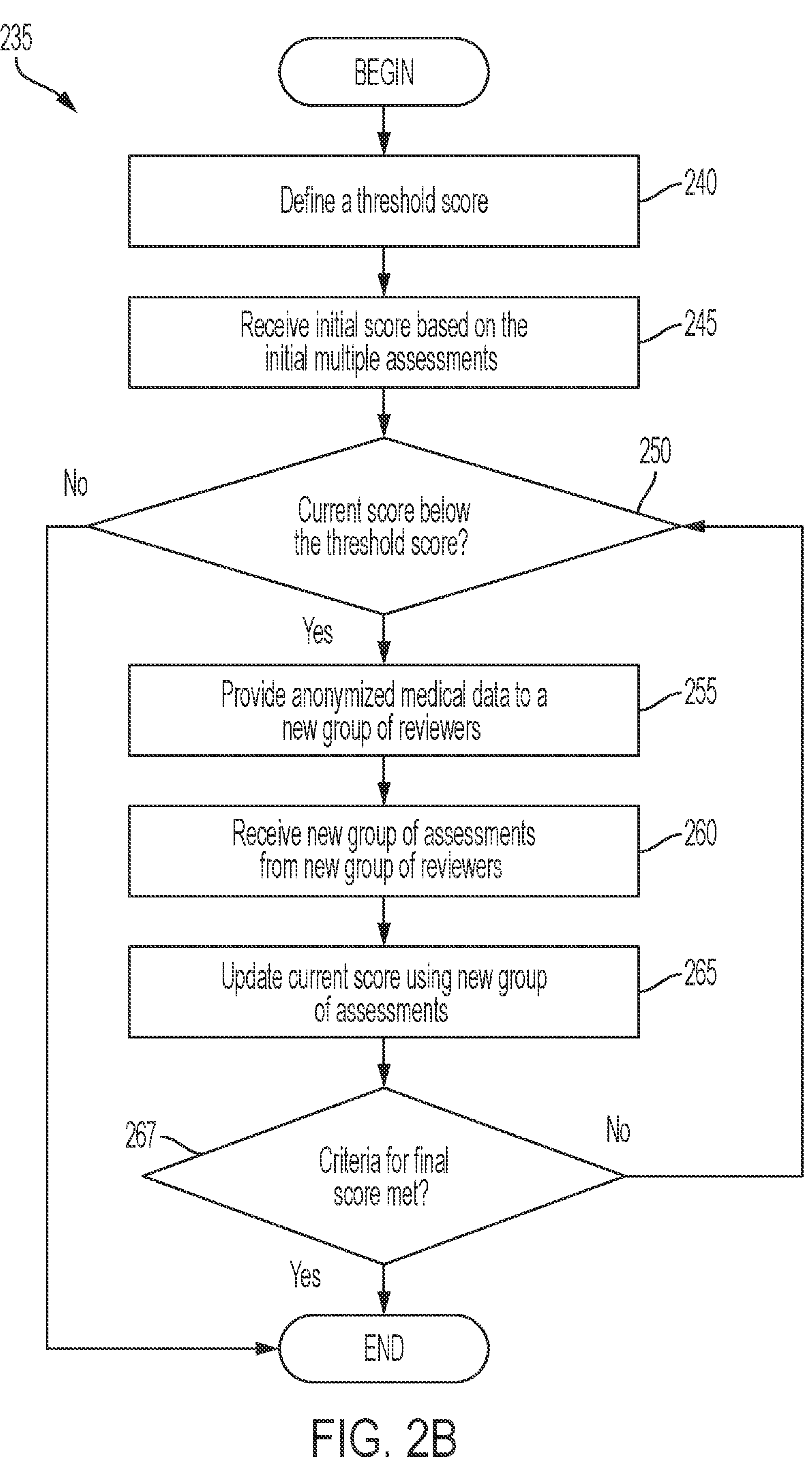
FIG. 2B shows a process performed in some embodiments by a score generator.

FIG. 2B shows a process 235, performed in some embodiments by a score generator. In some embodiments, the process 235 may be performed by the score generator 140 of the system 100 of FIG. 1, which is described above. For example, the process 235 may be performed as part of operation 225 of process 200.

The process begins at 240 by defining a threshold score, such that a score (e.g., score 184) above the threshold score indicates the quality of the treatment (e.g., treatment 104) is a valid or acceptable treatment and a score below the threshold score indicates the quality of the treatment is an invalid or unnacceptable treatment.

At 245, the process 235 receives the current score (e.g., score 184). During the initial execution of process 235, the current score will be the score that was previously generated from an initial group of assessments (e.g., assessments 174) that were generated by an initial group of reviewers (e.g., a subset of reviewers 110) from anonymized medical data (e.g., anonymized medical data 164). In some embodiments, operation 245 of process 235 is executed during or after operation 225 of process 200, which is described above.

At 250, the process 235 determines whether the current score is below the threshold score. If the process 235 determines that the current score is not below the threshold score, then the treatment is valid and/or acceptable, and the process 235 ends. If the process 235 determines that the current score is equal to or above the threshold score, the process 235 continues to 255, which is described below.

At 255, the process 235 provide the same anonymized medical data used to generate the initial group of assessments, to a new group of reviewers (e.g., a different subset of reviewers 110), and at 260, receives from the new group of reviewers, a new group of assessments (e.g., assessments 174) of the anonymized medical data. The process 235 may retrieve the anonymized medical data from a storage (e.g., de-identified storage 125).

At 265, the process 235 updates the current score based on the new group of assessments. In some embodiments, the process 235 updates the current score by generating a group of scores, each corresponding to one of the new group of assessments. The process 200 combines a group of scores from the previous assessments with the subsequent group of scores into a single new score and replaces the old current score with the new score.

At 267, the process 235 determines if a criteria for finalizing the score has been met. The criteria may be, for example, that the total number of reviewers has met or exceeded a predefined maximum number of reviewers. The total number of reviewers may be defined as the number of reviewers that initially reviewed the anonymized medical data, plus the number of new reviewers to whom the anonymized medical data was provided. As another example, the criteria may be that the number of iterations (e.g., from operation 250 above) has exceeded a predefined number of iterations. In some embodiments, the criteria may be a combination of multiple criteria, of which any single one must be satisfied, or of which all must be satisfied.

If the process 235 determines that the criteria has been met, the process 235 ends. If the process 235 determines that the criteria has not been met, then the process 235 returns to operation 250, which was described above.

As a non-limiting example, the initial number of reviewers may be five, and the total number of new reviewers may be ten, resulting in two iterations before process 235 ends.

As another non-limiting example, the initial number of reviewers may be seventy-five, and the predefined number of iterations is zero, resulting in a total number of reviewers being seventy-five before process 235 ends.

Figure 2C:
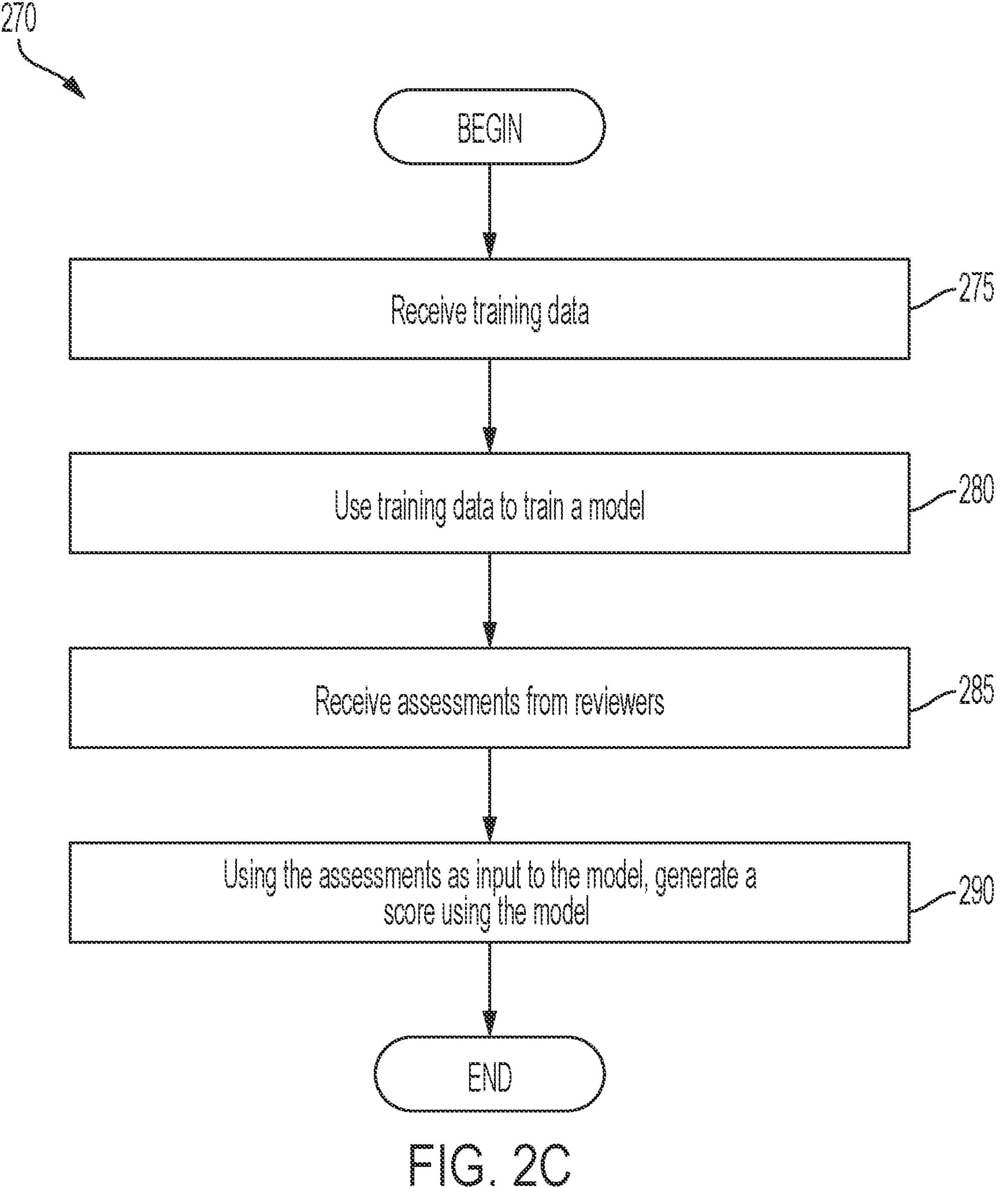
FIG. 2C shows a process for training a scoring model, performed by a system for peer review of some embodiments.

FIG. 2C shows a process 270 for training a scoring model, performed by a system for peer review of some embodiments. In some embodiments, the process 270 may be performed by the system 100 of FIG. 1, which is described above. At least a portion of the process 270 may be performed in some embodiments by a score generator, such as the score generator 240, which is described above.

The process 270 begins at 275 by receiving training data, the training data including descriptions of multiple previous treatments of multiple previous patients. The training data further includes corresponding previous scores (e.g., score 184), that represent the quality of the previous treatments.

At 280, the process 270 trains a model (e.g., model 190) using the training data, resulting in a trained model. In some embodiments, the model may be one of a clustering model (e.g., k-means), a neural network model (e.g., a convolutional neural network), a large language model (LLM), or other type of machine-learning (ML) or artificial intelligence (AI) model.

At 285, the process 270 receives multiple assessments (e.g., assessments 174) from multiple reviewers (e.g., reviewers 110). In some embodiments, operation 285 of process 270 is executed during or after operation 220 of process 200, which is described above.

At 290, the process 270 uses the assessments as inputs to the trained model and generates a score (e.g., score 184). In some embodiments, operation 290 of process 270 is executed during or after operation 225 of process 200, which is described above. The process 270 then ends.

Figure 3:
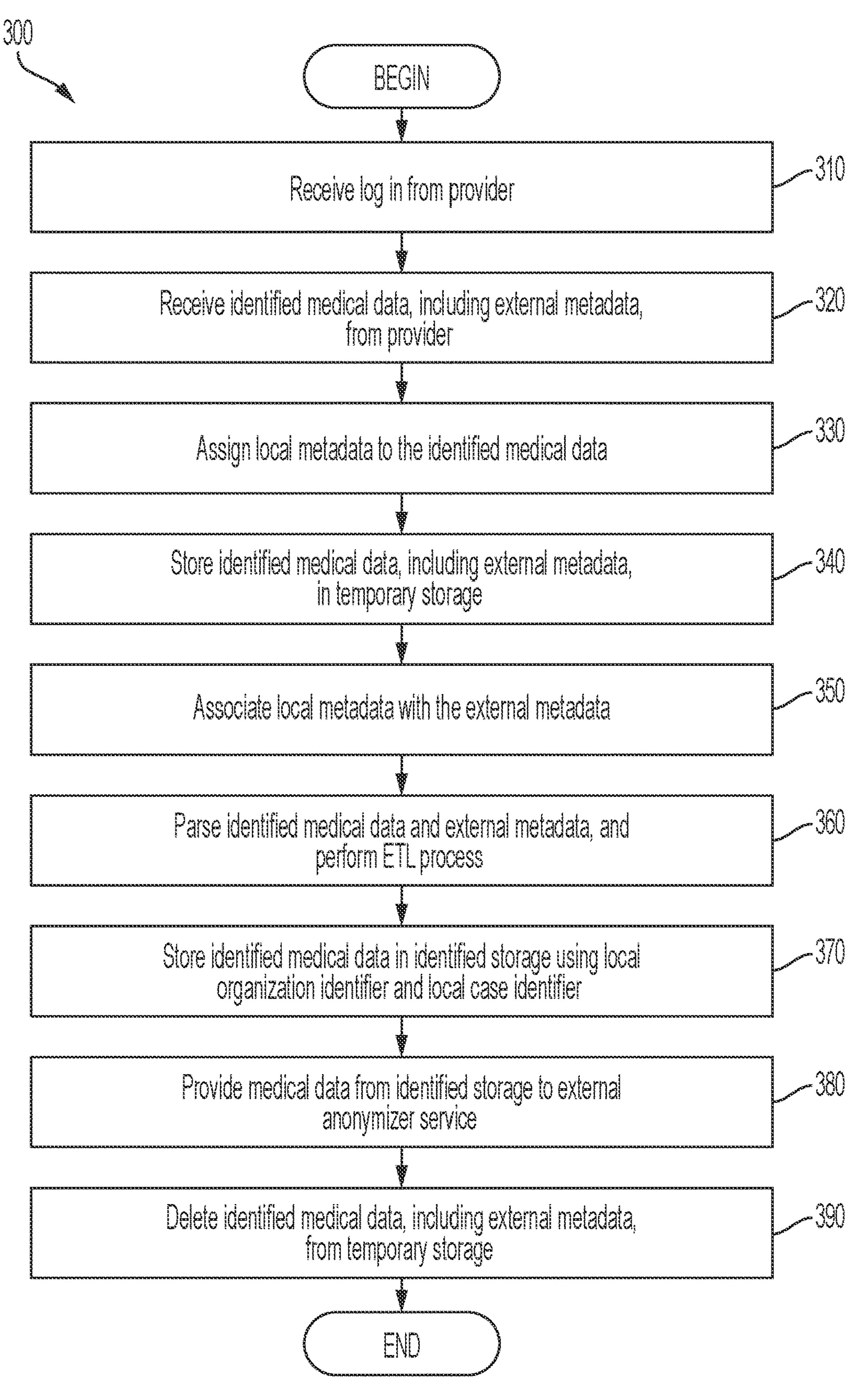
FIG. 3 shows a process for anonymizing medical data, performed by a system for peer review of some embodiments.

FIG. 3 shows a process 300 for anonymizing medical data, performed by a system for peer review of some embodiments. In some embodiments, the process 300 may be performed by the system 100 of FIG. 1, which is described above.

The process 300 begins at 310, by receiving a login from a medical provider (e.g., medical provider 108).

At 320, the process 300 receives, from the medical provider, identified medical data (e.g., identified medical data 114) for a patient (e.g., patient 106). The identified medical data includes external metadata that includes, but is not limited to, an external patient identifier, an external provider identifier, and a case date. The external patient/provider identifiers are assigned by the medical provider and can be used to identify the patient and/or the medical provider.

At 330, the process 300 assigns local metadata to the identified medical data, including but not limited to one or more of a local organization identifier, a local case identifier, a local patient identifier, and a local provider identifier. These local identifiers are internal to the peer review system and unknown to the medical provider or the patient.

At 340, the process 300 stores the identified medical data, including the external metadata, in a temporary storage (e.g., temporary storage 115).

At 350, the process 300 associates the local metadata with the external metadata. For example, the process 300 associates the local identifiers with the case date and the external patient and provider identifiers. These associations may be stored, for example, in a database of the peer review system. These associations are not visible to the medical provider or the patient since they are internal to the peer review system.

At 360, the process 300 parses the identified medical data and external metadata that is stored in the temporary storage, to extract, transform, and load (ETL) the identified medical data and the external metadata into a structured format (e.g., a file format, a data structure, or a database record).

At 370, the process 300 stores the extracted identified medical data in an identified storage (e.g., encrypted storage 120) using one or more of the identifiers in the local metadata. In other words, the identified medical data is stored only using one or more of the local identifiers for identification (e.g., including one or more of the local identifiers in a filename as a prefix or a suffix).

At 380, the process 300 provides the identified medical data from the identified storage to an external anonymizer service.

At 390, the process 300 deletes the identified medical data, including the external metadata, from the temporary storage. The process 300 then ends.

Figure 4:
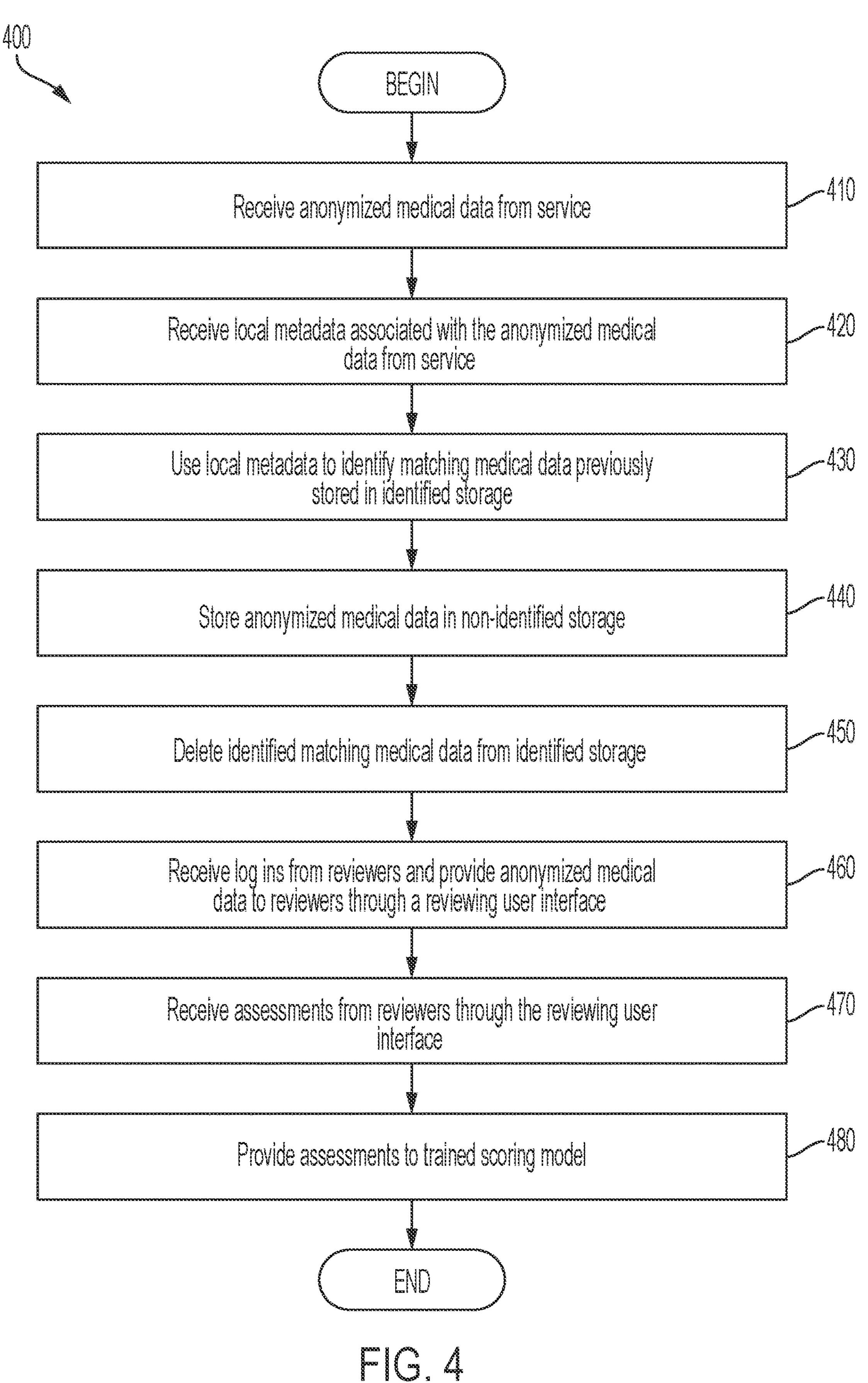
FIG. 4 shows a process performed by a system for peer review of some embodiments.

FIG. 4 shows a process 400 performed by a system for peer review of some embodiments. In some embodiments, the process 400 may be performed by the system 100 of FIG. 1, which is described above. At least a portion of the process 400 may be performed in some embodiments by a score generator, such as the score generator 240, which is described above. In some embodiments, the process 400 is performed after performing process 300, which is described above.

The process 400 begins at 410 by receiving, from an anonymizer service (e.g., anonymizer service 155), anonymized medical data (e.g., anonymized medical data 164).

At 420, the process 400 receives from the anonymizer service, local metadata associated with the anonymized medical data, including a local organization identifier, a local case identifier, a local patient identifier, and a local provider identifier. In some embodiments, at least a portion of the local metadata is assigned to the anonymized medical data by the peer review system. In some embodiments, at least a portion of the local metadata is assigned to the anonymized medical data by the anonymizer service.

At 430, the process 400 uses the local metadata to identify matching medical data previously stored in identified storage (e.g., encrypted storage 120). The identified matching medical data is associated with the anonymized medical data. This association may be stored, for example, in a database of the peer review system. These associations are not visible to the medical provider or the patient since they are internal to the peer review system.

At 440, the process 400 stores the anonymized medical data in a de-identified storage (e.g., de-identified storage 125).

At 450, the process 400 deletes the identified matching medical data from the identified storage.

At 460, the process 400 receives log ins from multiple reviewers (e.g., reviewers 110), and provides the anonymized medical data to the reviewers through a reviewing user interface.

At 470, the process 400 receives assessments (e.g., assessments 174) from the reviewers through the reviewing user interface.

At 480, the process 400 provides the assessments to a trained scoring model (e.g., model 190). The process 400 then ends.

Figure 5:
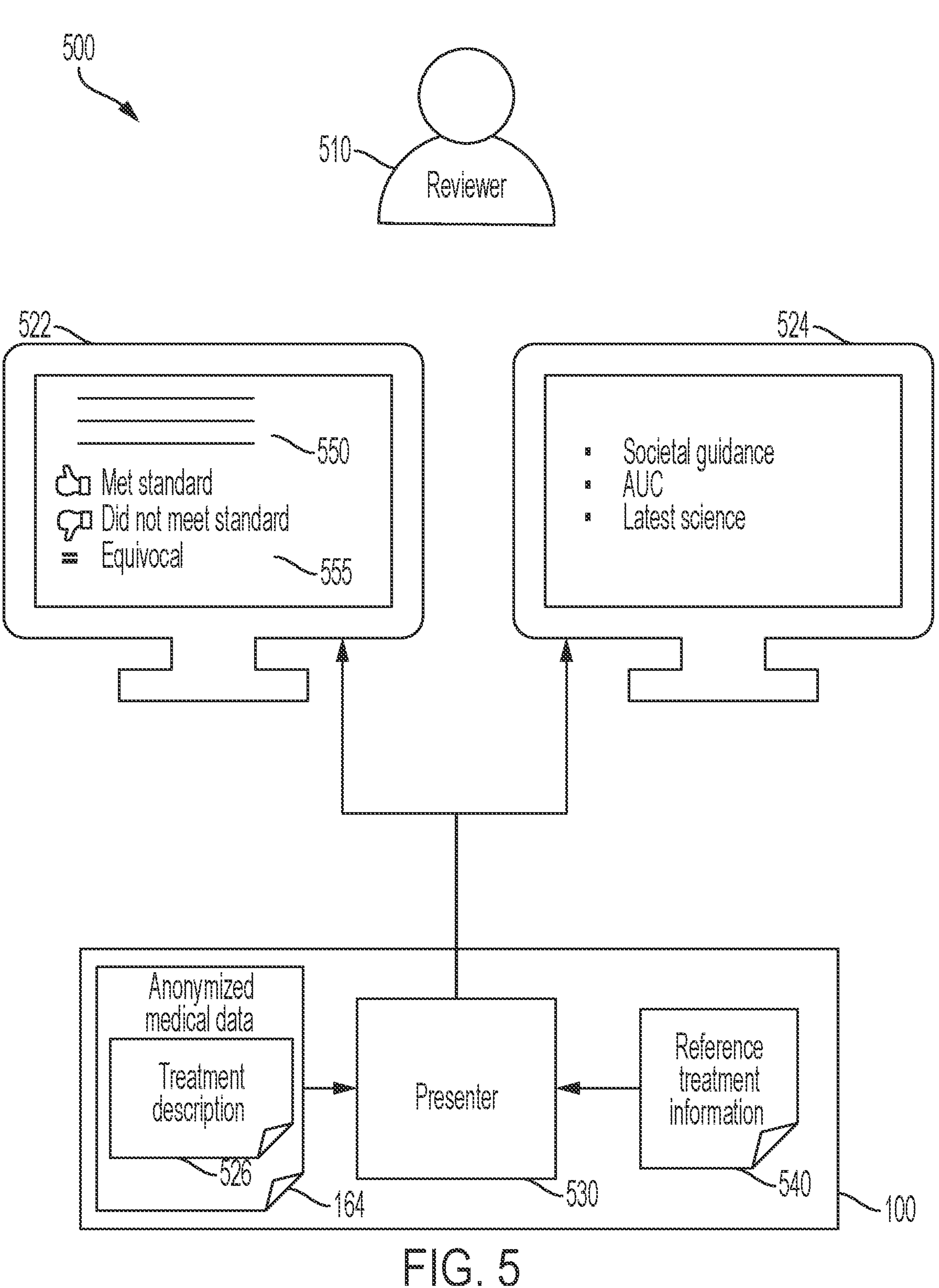
FIG. 5 shows a user interface for peer review, according to some embodiments.

FIG. 5 shows a user interface 500 for peer review, according to some embodiments. In this example, the user interface 500 is coupled to the peer review system 100 described above in FIG. 1. A peer reviewer 510 accesses anonymized medical data 164 of the patient 106 (not shown in FIG. 5), provided from the peer review system 100 using a first display 522 and a second display 524. The first display 522 and the second display 524 are communicatively connected to the peer review system 100. In this example, the anonymized medical data 164 includes a description 526 of the treatment 104 of the patient 106 by the medical provider 108 (not shown in FIG. 5).

In some embodiments, the system 100 further includes a presenter 530 that receives and parses the anonymized medical data 164, and provides information based on the anonymized medical data 164 to the reviewer 510 on either the first display 522, the second display 524, or both. In some embodiments, the presenter 530 further receives and parses reference treatment information 540, at least a portion of which may also be presented to the reviewer 510 on either the first display 522, the second display 524, or both. In some embodiments, the presenter 530 is configured by executing with a processor (not shown in FIG. 5), a set of instructions stored in a non-transitory computer readable medium (not shown in FIG. 5).

In some embodiments, the first display 522 is used to display the description 526 of the treatment 104. The description 526 of the treatment 104 may be presented in portions, along with user interface elements that allow the reviewer 510 to comment upon or rate each portion. The user interface elements associated with each portion of the description 526 may include, but are not limited to, text entry fields, checkboxes, radio buttons, drop down lists, toggles, ratings, Yes/No buttons, and thumbs up/down buttons.

In the example of FIG. 5, the first display 522 shows a portion 550 of the description 526 of the treatment 104, and a user interface element 550 that allows the reviewer 510 to indicate their agreement with a thumbs-up, disagreement with a thumbs-down, and equivocal opinion with an equals sign. Other portions (not shown in FIG. 5) of the description 526 may be associated with different types of user interface elements.

In the example of FIG. 5, the second display 524 shows a portion 560 of the reference treatment information 540. In this example, the portion 560 may include, but is not limited to, societal guidance, graphical data such as an area under a receiver operating characteristic curve (AUC), and summaries of the latest scientific and/or clinical findings. In some embodiments, the portion 560 may be contextual, and change depending on the portion 550 of the description being shown on the first display 522.

Figure 6:
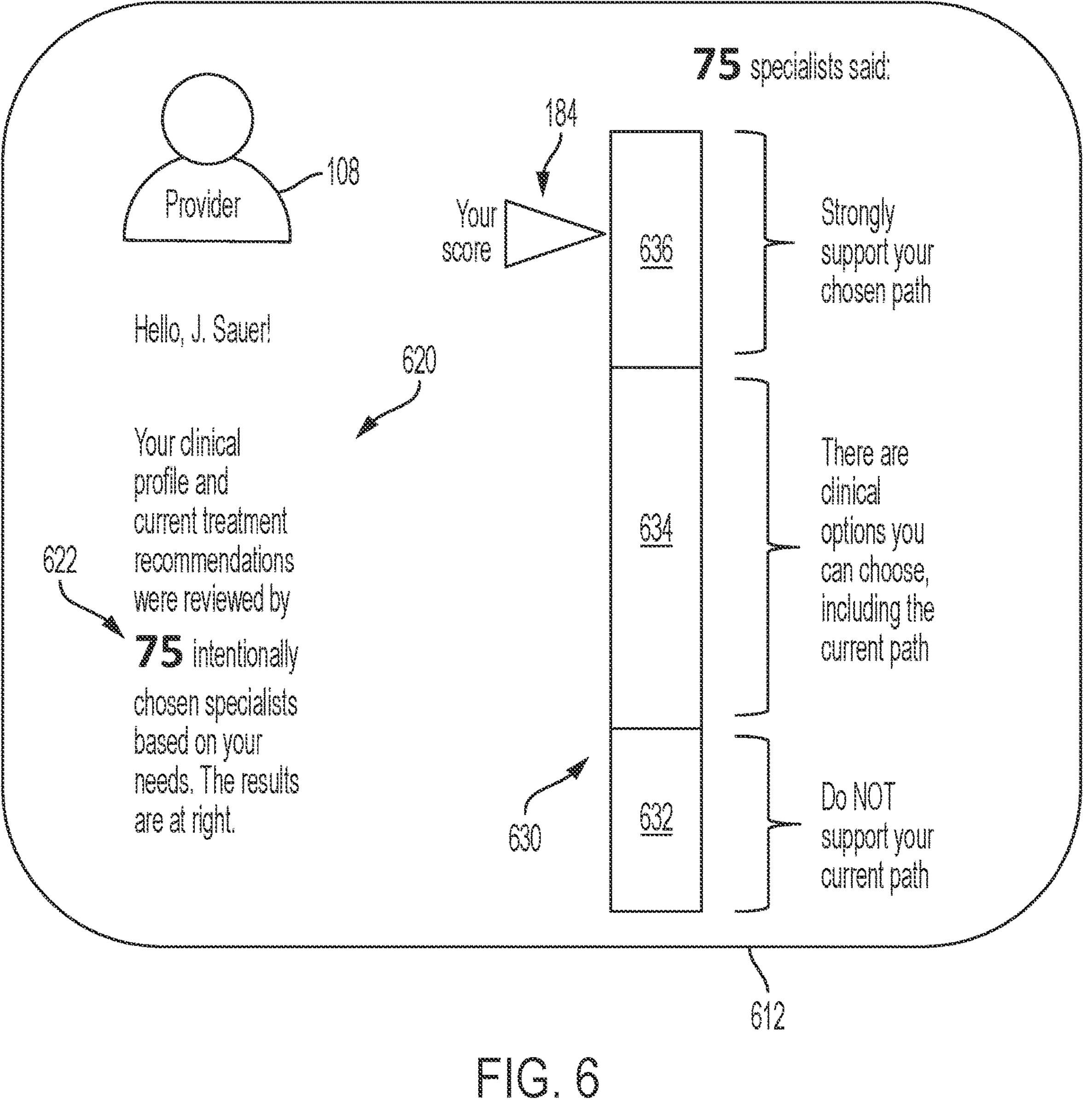
FIG. 6 shows an example of a report provided in some embodiments by the system of FIG. 1.

FIG. 6 shows an example of a report 612 provided in some embodiments by the system 100 to the medical provider 108. The report 612 may be displayed to the medical provider 108 upon login to the system 100, or may be provided to the medical provider 108 as a message, an email, a link to a webpage, etc.

In this example, the report 612 includes a summary 620 that provides information about the review. For example, the summary 620 includes the number 622 of reviewers who contributed to the report 612. The report 612 also includes a numeric scale 630, against which the score 184 may be compared. The scale 630 may be divided into regions 632, 634, 636 to assist the medical provider 108 in interpreting the score 684. In this example, a score in the lower region 632 of the scale 630 indicates that the treatment 104 was not generally supported by the reviewers. A score in the middle region 634 of the scale 630 indicates that the treatment 104 was acceptable, among other clinical options. A score in the top region 636 of the scale 630 indicates that the treatment 104 is strongly supported by the reviewers. In this example, the score 184 falls into the top region 636, indicating that the reviewers were generally in strong agreement with the treatment 104.

In some embodiments, the regions of the scale 630 may be color coded. For example, in some such embodiments, the lower region 632 may be colored red, the middle region 634 may be colored yellow, and the top region 636 may be colored green. Other coloring schemes, shading schemes, or different visualization schemes are also contemplated, including but not limited to different colors and grayscale.

In some embodiments, the scale 630 may range from zero to one hundred, the region 632 may range from zero to twenty-five, the region 634 may range from twenty-six to seventy-five, and the region 636 may range from seventy-six to one hundred.

In some embodiments, the scale 630 may range from zero percent to one hundred percent, the region 632 may range from zero percent to thirty nine percent, the region 634 may range from forty percent to seventy nine percent, and the region 636 may range from eighty percent to one hundred percent.

In some embodiments, the report 612 further includes a description (not shown in FIG. 6) of differences between the treatment 104 and an optimal treatment consensus.

The system may, in some embodiments, include a number of components, each of which may be implemented on a server or on an end-user device. In some cases, a subset of the components may execute on a user device (e.g., a mobile application on a cell phone, a webpage running within a web browser, a local application executing on a personal computer, etc.) and another subset of the components may execute on a server (a physical machine, virtual machine, or container, etc., which may be located at a datacenter, a cloud computing provider, a local area network, etc.).

The components of the system may be implemented in some embodiments as software programs or modules, which are described in more detail below. In other embodiments, some or all of the components may be implemented in hardware, including in one or more signal processing and/or application specific integrated circuits. While the components are shown as separate components, two or more components may be integrated into a single component. Also, while many of the components' functions are described as being performed by one component, the functions may be split among two or more separate components.

In addition, at least one figure conceptually illustrates a process. The specific operations of this process may not be performed in the exact order shown and described. The specific operations may not be performed in one continuous series of operations, and different specific operations may be performed in different embodiments. Furthermore, the process could be implemented using several sub-processes, or as part of a larger macro process.

Figure 7:
FIG. 7 conceptually illustrates an electronic system with which some embodiments of the invention are implemented.
Figure 7:
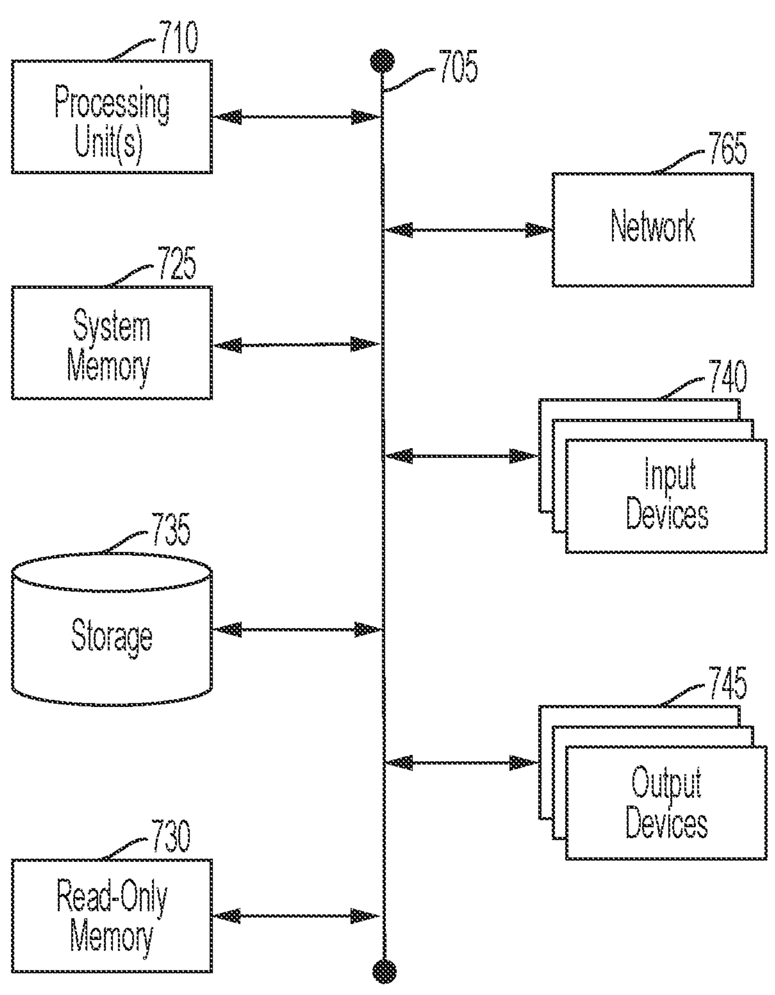

FIG. 7 conceptually illustrates an electronic system 700 with which some embodiments of the invention are implemented. The electronic system 700 can be used to execute any of the control and/or compiler systems described above in some embodiments. The electronic system 700 may be a computer (e.g., a desktop computer, personal computer, tablet computer, server computer, mainframe, a blade computer etc.), phone, PDA, or any other sort of electronic device. Such an electronic system includes various types of computer readable media and interfaces for various other types of computer readable media. Electronic system 700 may include one or more of a bus 705, processing unit(s) 710, a system memory 725, a read-only memory 730, a permanent storage device 735, input devices 740, and output devices 745.

The bus 705 collectively represents all system, peripheral, and chipset buses that communicatively connect the numerous internal devices of the electronic system 700. For instance, the bus 705 communicatively connects the processing unit(s) 710 with the read-only memory 730, the system memory 725, and the permanent storage device 735.

From these various memory units, the processing unit(s) 710 retrieves instructions to execute and data to process in order to execute the processes of the invention. The processing unit(s) may be a single processor or a multi-core processor in different embodiments.

The read-only-memory 730 stores static data and instructions that are needed by the processing unit(s) 710 and other modules of the electronic system. The permanent storage device 735, on the other hand, is a read-and-write memory device. This device is a non-volatile memory unit that stores instructions and data even when the electronic system 700 is off. Some embodiments of the invention use a mass-storage device (such as a magnetic or optical disk and its corresponding disk drive) as the permanent storage device 735.

Other embodiments use a removable storage device (such as a floppy disk, flash drive, etc.) as the permanent storage device. Like the permanent storage device 735, the system memory 725 is a read-and-write memory device. However, unlike storage device 735, the system memory is a volatile read-and-write memory, such a random-access memory. The system memory stores some of the instructions and data that the processor needs at runtime. In some embodiments, the invention's processes are stored in the system memory 725, the permanent storage device 735, and/or the read-only memory 730. From these various memory units, the processing unit(s) 710 retrieves instructions to execute and data to process in order to execute the processes of some embodiments.

The bus 705 also connects to the input devices 740 and output devices 745. The input devices enable the user to communicate information and select commands to the electronic system. The input devices 740 include alphanumeric keyboards and pointing devices (also called "cursor control devices"). The output devices 745 display images generated by the electronic system. The output devices include printers and display devices, such as cathode ray tubes (CRT) or liquid crystal displays (LCD). Some embodiments include devices such as a touchscreen that function as both input and output devices.

Finally, as shown in FIG. 7, bus 705 also couples electronic system 700 to a network 765 through a network adapter (not shown). In this manner, the computer can be a part of a network of computers (such as a local area network ("LAN"), a wide area network ("WAN"), or an Intranet, or a network of networks, such as the Internet. Any or all components of electronic system 700 may be used in conjunction with the invention.

As used in this specification, the terms "computer", "server", "processor", and "memory" all refer to electronic or other technological devices. These terms exclude people or groups of people. As used in this specification, the terms "computer readable medium," "computer readable media," and "machine readable medium," etc. are entirely restricted to tangible, physical objects that store information in a form that is readable by a computer. These terms exclude any wireless signals, wired download signals, and any other ephemeral signals.

The term "computer" is intended to have a broad meaning that may be used in computing devices such as, e.g., but not limited to, standalone or client or server devices. The computer may be, e.g., (but not limited to) a personal computer (PC) system running an operating system such as, e.g., (but not limited to) MICROSOFT® WINDOWS® available from MICROSOFT® Corporation of Redmond, Wash., U.S.A. or an Apple computer executing MAC® OS from Apple® of Cupertino, Calif., U.S.A. However, the invention is not limited to these platforms. Instead, the invention may be implemented on any appropriate computer system running any appropriate operating system. In one illustrative embodiment, the present invention may be implemented on a computer system operating as discussed herein. The computer system may include, e.g., but is not limited to, a main memory, random access memory (RAM), and a secondary memory, etc. Main memory, random access memory (RAM), and a secondary memory, etc., may be a computer-readable medium that may be configured to store instructions configured to implement one or more embodiments and may comprise a random-access memory (RAM) that may include RAM devices, such as Dynamic RAM (DRAM) devices, flash memory devices, Static RAM (SRAM) devices, etc.

The secondary memory may include, for example, (but not limited to) a hard disk drive and/or a removable storage drive, representing a floppy diskette drive, a magnetic tape drive, an optical disk drive, a read-only compact disk (CD-ROM), digital versatile discs (DVDs), flash memory (e.g., SD cards, mini-SD cards, micro-SD cards, etc.), read-only and recordable Blu-Ray® discs, etc. The removable storage drive may, e.g., but is not limited to, read from and/or write to a removable storage unit in a well-known manner. The removable storage unit, also called a program storage device or a computer program product, may represent, e.g., but is not limited to, a floppy disk, magnetic tape, optical disk, compact disk, etc. which may be read from and written to the removable storage drive. As will be appreciated, the removable storage unit may include a computer usable storage medium having stored therein computer software and/or data.

In some embodiments, the secondary memory may include other similar devices for allowing computer programs or other instructions to be loaded into the computer system. Such devices may include, for example, a removable storage unit and an interface. Examples of such may include a program cartridge and cartridge interface (such as, e.g., but not limited to, those found in video game devices), a removable memory chip (such as, e.g., but not limited to, an erasable programmable read only memory (EPROM), or programmable read only memory (PROM) and associated socket, and other removable storage units and interfaces, which may allow software and data to be transferred from the removable storage unit to the computer system.

Some embodiments include electronic components, such as microprocessors, storage and memory that store computer program instructions in a machine-readable or computer-readable medium (alternatively referred to as computer-readable storage media, machine-readable media, or machine-readable storage media). The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

The computer may also include an input device may include any mechanism or combination of mechanisms that may permit information to be input into the computer system from, e.g., a user. The input device may include logic configured to receive information for the computer system from, e.g., a user. Examples of the input device may include, e.g., but not limited to, a mouse, pen-based pointing device, or other pointing device such as a digitizer, a touch sensitive display device, and/or a keyboard or other data entry device (none of which are labeled). Other input devices may include, e.g., but not limited to, a biometric input device, a video source, an audio source, a microphone, a web cam, a video camera, and/or another camera. The input device may communicate with a processor either wired or wirelessly.

The computer may also include output devices which may include any mechanism or combination of mechanisms that may output information from a computer system. An output device may include logic configured to output information from the computer system. Embodiments of output device may include, e.g., but not limited to, display, and display interface, including displays, printers, speakers, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), etc. The computer may include input/output (I/O) devices such as, e.g., (but not limited to) communications interface, cable and communications path, etc. These devices may include, e.g., but are not limited to, a network interface card, and/or modems. The output device may communicate with processor either wired or wirelessly. A communications interface may allow software and data to be transferred between the computer system and external devices.

The term "processor" is intended to have a broad meaning that includes one or more processors, such as, e.g., but not limited to, that are connected to a communication infrastructure (e.g., but not limited to, a communications bus, cross-over bar, interconnect, or network, etc.). The term processor may include any type of processor, microprocessor and/or processing logic that may interpret and execute instructions, including application-specific integrated circuits (ASICs) and field-programmable gate arrays (FPGAs). The processor may comprise a single device (e.g., for example, a single core) and/or a group of devices (e.g., multi-core). The processor may include logic configured to execute computer-executable instructions configured to implement one or more embodiments. The instructions may reside in main memory or secondary memory. The processor may also include multiple independent cores, such as a dual-core processor or a multi-core processor. The processors may also include one or more graphics processing units (GPU) which may be in the form of a dedicated graphics card, an integrated graphics solution, and/or a hybrid graphics solution. Various illustrative software embodiments may be described in terms of this illustrative computer system. After reading this description, it will become apparent to a person skilled in the relevant art(s) how to implement the invention using other computer systems and/or architectures.

The term "storage" is intended to have a broad meaning that includes removable storage drive, a hard disk installed in hard disk drive, flash memories, removable discs, non-removable discs, etc. In addition, it should be noted that various electromagnetic radiation, such as wireless communication, electrical communication carried over an electrically conductive wire (e.g., but not limited to twisted pair, CAT5, etc.) or an optical medium (e.g., but not limited to, optical fiber) and the like may be encoded to carry computer-executable instructions and/or computer data that embodiments of the invention on e.g., a communication network. These computer program products may provide software to the computer system. It should be noted that a computer-readable medium that comprises computer-executable instructions for execution in a processor may be configured to store various embodiments of the present invention.

The term "network" is intended to include any communication network, including a local area network ("LAN"), a wide area network ("WAN"), an Intranet, or a network of networks, such as the Internet.

The term "software" is meant to include firmware residing in read-only memory or applications stored in magnetic storage, which can be read into memory for processing by a processor. Also, in some embodiments, multiple software inventions can be implemented as sub-parts of a larger program while remaining distinct software inventions. In some embodiments, multiple software inventions can also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

The model 190 of some embodiments is a multi-layer machine-trained network (e.g., a feed-forward neural network). Neural networks, also referred to as machine-trained networks, will be herein described. One class of machine-trained networks are deep neural networks with multiple layers of nodes. Different types of such networks include feed-forward networks, convolutional networks, recurrent networks, regulatory feedback networks, radial basis function networks, long-short term memory (LSTM) networks, and Neural Turing Machines (NTM). Multi-layer networks are trained to execute a specific purpose, including face recognition or other image analysis, voice recognition or other audio analysis, large-scale data analysis (e.g., for climate data), etc. In some embodiments, such a multi-layer network is designed to execute on a mobile device (e.g., a smartphone or tablet), an IoT device, a web browser window, etc.

Before a multi-layer network can be used to solve a particular problem, the network is put through a supervised training process that adjusts the network's configurable parameters (e.g., the weight coefficients, and additionally in some cases the bias factor). The training process iteratively selects different input value sets with known output value sets. For each selected input value set, the training process typically (1) forward propagates the input value set through the network's nodes to produce a computed output value set and then (2) back-propagates a gradient (rate of change) of a loss function (output error) that quantifies the difference between the input set's known output value set and the input set's computed output value set, in order to adjust the network's configurable parameters (e.g., the weight values).

In some embodiments, training the neural network involves defining a loss function (also called a cost function) for the network that measures the error (i.e., loss) of the actual output of the network for a particular input compared to a pre-defined expected (or ground truth) output for that particular input. During one training iteration (also referred to as a training epoch), a training dataset is first forward-propagated through the network nodes to compute the actual network output for each input in the data set. Then, the loss function is back-propagated through the network to adjust the weight values in order to minimize the error (e.g., using first-order partial derivatives of the loss function with respect to the weights and biases, referred to as the gradients of the loss function). The accuracy of these trained values is then tested using a validation dataset (which is distinct from the training dataset) that is forward propagated through the modified network, to see how well the training performed. If the trained network does not perform well (e.g., have error less than a predetermined threshold), then the network is trained again using the training dataset. This cyclical optimization method for minimizing the output loss function, iteratively repeated over multiple epochs, is referred to as stochastic gradient descent (SGD).

Further embodiments of the invention are provided by the subject matter of the following clauses.

1. A method for peer review, comprising: receiving a request from a medical provider, said request comprising identified medical data that is uniquely associated with a patient and that is uniquely associated with said medical provider; generating anonymized medical data by normalizing said identified medical data to remove any association with said patient and to remove any association with said medical provider, resulting in anonymized medical data; providing said anonymized medical data to a plurality of reviewers; receiving, from said plurality of reviewers, a plurality of assessments of said anonymized medical data; generating a score based on said plurality of assessments; and providing a report comprising said score to said medical provider, wherein said score represents a quality of a treatment of said patient by said medical provider.
2. The method of clause 1, wherein said report is an anonymized report that does not identify any of said plurality of reviewers.
3. The method of any of clauses 1 and 2, wherein the request further comprises at least one of a date, a case number, and an account identifier.
4. The method of clause 3, wherein generating said anonymized medical data comprises at least one of replacing said account identifier with an anonymized account identifier and replacing said case number with an anonymized case number.
5. The method of any of clauses 1-4, wherein said identified medical data comprises a description of said treatment, and said plurality of assessments comprise a plurality of assessments of said quality of said treatment based on said description.
6. The method of clause 5, wherein said description of said treatment comprises a description of a medical condition of said patient, said treatment is for said medical condition, and said report further comprises a comparison between said treatment and an optimal treatment for said medical condition.
7. The method of any of clauses 1-6, further comprising validating said request to determine whether said identified medical data is complete, prior to generating said anonymized medical data.
8. The method of any of clauses 1-7, further comprising validating said anonymized medical data to determine whether said anonymized medical data is complete, prior to providing said anonymized medical data to said plurality of reviewers.
9. The method of any of clauses 1-8, wherein said identified medical data is uniquely associated with said patient using a patient identifier, and normalizing said identified medical data to remove any association with said patient comprises removing all occurrences of said patient identifier from said identified medical data.
10. The method of clause 9, wherein removing all occurrences of said patient identifier comprises replacing said patient identifier with an anonymized patient identifier.
11. The method of any of clauses 1-10, wherein said medical provider is a person that is capable of providing treatment to said patient, and wherein said identified medical data is uniquely associated with said medical provider using a provider identifier, and wherein normalizing said identified medical data to remove any association with said medical provider comprises removing all occurrences of said provider identifier from said identified medical data.
12. The method of clause 11, wherein removing all occurrences of said provider identifier comprises replacing said provider identifier with an anonymized provider identifier.
13. The method of any of clauses 1-12, wherein said identified medical data is uniquely associated with a medical organization and generating said anonymized medical data comprises further normalizing said identified medical data to remove any association with said medical organization.
14. The method of clause 13, wherein said identified medical data is uniquely associated with said medical organization using an organization identifier, and wherein normalizing said identified medical data to remove any association with said medical organization comprises removing all occurrences of said organization identifier from said identified medical data.
15. The method of any of clauses 1-14, wherein generating anonymized medical data comprises: providing said identified medical data to a service; and receiving, from said service, said anonymized medical data.
16. The method of clause 15, further comprising: storing the identified medical data in a first storage; storing the anonymized medical data in a second storage; and deleting said identified medical data from the first storage, wherein said identified medical data is provided to said service from said first storage, and said anonymized medical data is provided to said plurality of reviewers from said second storage.
17. The method of any of clauses 1-16, wherein generating said score based on said plurality of assessments comprises combining said plurality of assessments into an aggregate assessment and generating said score based on said aggregate assessment.
18. The method of any of clauses 1-17, wherein generating said score based on said plurality of assessments comprises generating a plurality of initial scores, each corresponding to one of said plurality of assessments, and combining said plurality of initial scores into said score.
19. The method of clause 18, wherein said plurality of reviewers is a first plurality of reviewers, said score is a first score, and said plurality of assessments is a first plurality of assessments, and wherein generating said first score based on said first plurality of assessments further comprises: defining a threshold score, wherein a score above said threshold score indicates said quality of said treatment is a valid treatment and a score below said threshold score indicates said quality of said treatment is an invalid treatment; making a determination that said first score is below said threshold score; and based on said determination, providing said anonymized medical data to a second plurality of reviewers; receiving, from said second plurality of reviewers, a second plurality of assessments of said anonymized medical data; and updating said first score based on said first plurality of assessments and said second plurality of assessments.

20. The method of clause 19, wherein said plurality of initial scores is a first plurality of initial scores, and updating said first score comprises: generating a second plurality of initial scores, each corresponding to one of said second plurality of assessments; combining said first plurality of initial scores and said second plurality of initial scores into a second score; and replacing said first score with said second score.
21. The method of any of clauses 1-20, wherein generating said score based on said plurality of assessments comprises: receiving training data, said training data comprising a plurality of descriptions of a plurality of previous treatments of a plurality of previous patients, and further comprising a corresponding plurality of previous scores, wherein said plurality of previous scores represent a quality of said plurality of previous treatments; training a model using said training data, resulting in a trained model; and providing said plurality of assessments to said trained model to generate said score.
22. A system for peer review, comprising: a processor; a storage, configured to receive a request from a medical provider, said request comprising identified medical data that is uniquely associated with a patient and that is uniquely associated with said medical provider; an anonymizer, configured to receive said identified medical data from said storage, generate anonymized medical data by normalizing said identified medical data to remove any association with said patient and to remove any association with said medical provider, resulting in anonymized medical data, and provide said anonymized medical data to a plurality of reviewers; a score generator, configured to receive, from said plurality of reviewers, a plurality of assessments of said anonymized medical data, and generate a score based on said plurality of assessments, wherein said score represents a quality of a treatment of said patient by said medical provider; a report generator, configured to receive said score from said score generator, and provide a report comprising said score to said medical provider; and a non-transitory computer readable medium storing a set of instructions, which when executed by said processor, configure said anonymizer, said score generator, and said report generator.
23. The system of clause 22, wherein said report generator is further configured to receive said plurality of assessments, and said report further comprises said plurality of assessments.
24. The system of any of clauses 22 and 23, wherein said anonymizer is an anonymizer service.
25. The system of any of clauses 22-24, wherein said storage is a first storage, said system further comprising: a second storage adapted for storing identified medical data; and parser configured to: extract said identified medical data from said first storage; transform said identified medical data to a particular format; and store said transformed identified medical data in said second storage, wherein said anonymizer is further configured to receive said transformed identified medical data from said second storage, and said set of instructions, when executed by said at least one processor, configure said parser.
26. The system of any of clauses 22-25, wherein said storage is a first storage, said system further comprising a second storage, adapted for storing anonymized medical data, wherein said anonymizer is further configured to store anonymized medical data in said second storage, and providing said anonymized medical data to said plurality of reviewers comprises providing said anonymized medical data from said second storage.
27. The system of any of clauses 22-26, wherein said report is an anonymized report that does not identify any of said plurality of reviewers.
28. The system of any of clauses 22-27, wherein the identified medical data further comprises at least one of a date, a case number, and an account identifier.
29. The system of clause 28, wherein said anonymizer is further configured to generate said anonymized medical data by at least one of replacing said account identifier with an anonymized account identifier and replacing said case number with an anonymized case number.
30. The system of any of clauses 22-29, wherein said identified medical data comprises a description of said treatment and said plurality of assessments comprise a plurality of assessments of said quality of said treatment based on said description.
31. The system of clause 30, wherein said description of said treatment comprises a description of a medical condition of said patient, said treatment is for said medical condition, and said report further comprises a comparison between said treatment and an optimal treatment for said medical condition.
32. The system of any of clauses 22-31, further comprising a validator configured to receive said request from said medical provider, validate said request to determine whether said identified medical data is complete, and, based on a determination that said identified medical data is complete, provide said request to said storage, wherein said storage is further configured to receive said request from said validator, and said set of instructions, when executed by said at least one processor, configure said validator.
33. The system of clause 32, wherein said validator is further configured to receive said anonymized medical data from said anonymizer, validate said anonymized medical data to determine whether said anonymized medical data is complete, and, based on a determination that said anonymized medical data is complete, provide said anonymized medical data to said plurality of reviewers, wherein said anonymizer is further configured to provide said anonymized medical data to said validator.
34. The system of any of clauses 22-33, wherein said identified medical data is uniquely associated with said patient using a patient identifier, and said anonymizer is further configured to remove all occurrences of said patient identifier from said identified medical data.
35. The system of clause 34, wherein removing all occurrences of said patient identifier comprises replacing said patient identifier with an anonymized patient identifier.
36. The system of any of clauses 22-35, wherein said medical provider is a person that is capable of providing treatment to said patient, said identified medical data is uniquely associated with said medical provider using a provider identifier, and said anonymizer is further configured to remove all occurrences of said provider identifier from said identified medical data.
37. The system of clause 36, wherein removing all occurrences of said provider identifier comprises replacing said provider identifier with an anonymized provider identifier.

38. The system of any of clauses 22-37, wherein said identified medical data is uniquely associated with a medical organization, and said anonymizer is further configured to remove any association with said medical organization.
39. The system of clause 38, wherein said identified medical data is uniquely associated with said medical organization using an organization identifier, and said anonymizer is further configured to remove all occurrences of said organization identifier from said identified medical data.
40. The system of any of clauses 22-39, wherein said score generator is further configured to combine said plurality of assessments into an aggregate assessment and generate said score based on said aggregate assessment.
41. The system of any of clauses 22-40, wherein said score generator is further configured to generate a plurality of initial scores, each corresponding to one of said plurality of assessments, and combine said plurality of initial scores into said score.
42. The system of clause 41, wherein said plurality of reviewers is a first plurality of reviewers, said score is a first score, and said plurality of assessments is a first plurality of assessments, and said score generator is further configured to: define a threshold score, wherein a score above said threshold score indicates said quality of said treatment is a valid treatment and a score below said threshold score indicates said quality of said treatment is an invalid treatment; make a determination that said first score is below said threshold score; based on said determination, direct said anonymizer to provide said anonymized medical data to a second plurality of reviewers; receive, from said second plurality of reviewers, a second plurality of assessments of said anonymized medical data; and update said first score based on said first plurality of assessments and said second plurality of assessments.
43. The system of clause 42, wherein said plurality of initial scores is a first plurality of initial scores, and said score generator is further configured to: generate a second plurality of initial scores, each corresponding to one of said second plurality of assessments; combine said first plurality of initial scores and said second plurality of initial scores into a second score; and replace said first score with said second score.
44. The system of any of clauses 22-43, wherein said score generator is further configured to: receive training data, said training data comprising a plurality of descriptions of a plurality of previous treatments of a plurality of previous patients, and further comprising a corresponding plurality of previous scores, wherein said plurality of previous scores represent a quality of said plurality of previous treatments; train a model using said training data, resulting in a trained model; and provide said plurality of assessments to said trained model to generate said score.
45. A non-transitory computer-readable medium storing a set of instructions for peer review, which when executed by a computer, configure the computer to: receive a request from a medical provider, said request comprising identified medical data that is uniquely associated with a patient and that is uniquely associated with said medical provider; generate anonymized medical data by normalizing said identified medical data to remove any association with said patient and to remove any association with said medical provider, resulting in anonymized medical data; provide said anonymized medical data to a plurality of reviewers; receive, from said plurality of reviewers, a plurality of assessments of said anonymized medical data; generate a score based on said plurality of assessments; and provide a report comprising said score to said medical provider, wherein said score represents a quality of a treatment of said patient by said medical provider.
46. The non-transitory computer-readable medium of clause 45, wherein said report is an anonymized report that does not identify any of said plurality of reviewers.
47. The non-transitory computer-readable medium of clauses 45 and 46, wherein the request further comprises at least one of a date, a case number, and an account identifier.
48. The non-transitory computer-readable medium of clause 47, wherein the set of instructions, when executed, further configure the computer to replace said account identifier with an anonymized account identifier and replace said case number with an anonymized case number.
49. The non-transitory computer-readable medium of any of clauses 45-48, wherein said identified medical data comprises a description of said treatment and said plurality of assessments comprise a plurality of assessments of said quality of said treatment based on said description.
50. The non-transitory computer-readable medium of clause 49, wherein said description of said treatment comprises a description of a medical condition of said patient, said treatment is for said medical condition, and said report further comprises a comparison between said treatment and an optimal treatment for said medical condition.
51. The non-transitory computer-readable medium of any of clauses 45-50, wherein the set of instructions, when executed, further configure the computer to validate said request to determine whether said identified medical data is complete, prior to generating said anonymized medical data.
52. The non-transitory computer-readable medium of any of clauses 45-51, wherein the set of instructions, when executed, further configure the computer to validate said anonymized medical data to determine whether said anonymized medical data is complete, prior to providing said anonymized medical data to said plurality of reviewers.
53. The non-transitory computer-readable medium of any of clauses 45-52, wherein said identified medical data is uniquely associated with said patient using a patient identifier, and wherein the set of instructions, when executed, further configure the computer to remove all occurrences of said patient identifier from said identified medical data.
54. The non-transitory computer-readable medium of clause 53, wherein removing all occurrences of said patient identifier comprises replacing said patient identifier with an anonymized patient identifier.
55. The non-transitory computer-readable medium of any of clauses 45-54, wherein said medical provider is a person that is capable of providing treatment to said patient, and wherein said identified medical data is uniquely associated with said medical provider using a provider identifier, and wherein the set of instructions, when executed, further configure the computer to remove all occurrences of said provider identifier from said identified medical data.

56. The non-transitory computer-readable medium of clause 55, wherein removing all occurrences of said provider identifier comprises replacing said provider identifier with an anonymized provider identifier.
57. The non-transitory computer-readable medium of any of clauses 45-56, wherein said identified medical data is uniquely associated with a medical organization and wherein the set of instructions, when executed, further configure the computer to further normalize said identified medical data to remove any association with said medical organization.
58. The non-transitory computer-readable medium of clause 57, wherein said identified medical data is uniquely associated with said medical organization using an organization identifier, and wherein the set of instructions, when executed, further configure the computer to remove all occurrences of said organization identifier from said identified medical data.
59. The non-transitory computer-readable medium of any of clauses 45-58, wherein the set of instructions, when executed, further configure the computer to: provide said identified medical data to a service; and receive, from said service, said anonymized medical data.
60. The non-transitory computer-readable medium of clause 59, wherein the set of instructions, when executed, further configure the computer to: store the identified medical data in a first storage; store the anonymized medical data in a second storage; and delete said identified medical data from the first storage, wherein said identified medical data is provided to said service from said first storage, and said anonymized medical data is provided to said plurality of reviewers from said second storage.
61. The non-transitory computer-readable medium of any of clauses 45-60, wherein the set of instructions, when executed, further configure the computer to combine said plurality of assessments into an aggregate assessment and generate said score based on said aggregate assessment.
62. The non-transitory computer-readable medium of any of clauses 45-61, wherein the set of instructions, when executed, further configure the computer to generate a plurality of initial scores, each corresponding to one of said plurality of assessments, and combine said plurality of initial scores into said score.
63. The non-transitory computer-readable medium of clause 62, wherein said plurality of reviewers is a first plurality of reviewers, said score is a first score, and said plurality of assessments is a first plurality of assessments, and wherein the set of instructions, when executed, further configure the computer to: define a threshold score, wherein a score above said threshold score indicates said quality of said treatment is a valid treatment and a score below said threshold score indicates said quality of said treatment is an invalid treatment; make a determination that said first score is below said threshold score; and based on said determination, provide said anonymized medical data to a second plurality of reviewers; receive, from said second plurality of reviewers, a second plurality of assessments of said anonymized medical data; and update said first score based on said first plurality of assessments and said second plurality of assessments.
64. The non-transitory computer-readable medium of clause 63, wherein said plurality of initial scores is a first plurality of initial scores, and wherein the set of instructions, when executed, further configure the computer to: generate a second plurality of initial scores, each corresponding to one of said second plurality of assessments; combine said first plurality of initial scores and said second plurality of initial scores into a second score; and replace said first score with said second score.
65. The non-transitory computer-readable medium of any of clauses 45-64, wherein the set of instructions, when executed, further configure the computer to: receive training data, said training data comprising a plurality of descriptions of a plurality of previous treatments of a plurality of previous patients, and further comprising a corresponding plurality of previous scores, wherein said plurality of previous scores represent a quality of said plurality of previous treatments; train a model using said training data, resulting in a trained model; and provide said plurality of assessments to said trained model to generate said score.

REFERENCES

All references cited anywhere in this specification, including the Background and Detailed Description sections, are incorporated by reference as if each had been individually incorporated.

JAMA. 2019; 322(15):1501-1509. doi:10.1001/jama.2019.13978

Cardiovascular Quality and Outcomes. 2014; 7:807-808

Further details on neural networks may be found in the following references, which are incorporated herein by reference in their entirety.

Nair, Vinod and Hinton, Geoffrey E., "Rectified linear units improve restricted Boltzmann machines," ICML, pp. 807-814, 2010.

He, Kaiming, Zhang, Xiangyu, Ren, Shaoqing, and Sun, Jian, "Delving deep into rectifiers: Surpassing human-level performance on imagenet classification," arXiv preprint arXiv:1502.01852, 2015.

Mayer, Nikolaus, Ilg, Eddy, Häusser, Philip, Fischer, Philipp, Cremers, Daniel, Dosovitskiy, Alexey, and Brox, Thomas, "A Large Dataset to Train Convolutional Networks for Disparity, Optical Flow, and Scene Flow Estimation," arXiv preprint arXiv:1512.02134, 2015.

He, Kaiming, Zhang, Xiangyu, Ren, Shaoqing, and Sun, Jian, "Deep Residual Learning for Image Recognition," arXiv preprint arXiv: 1512.03385, 2015.

The various embodiments described above are provided by way of illustration only and should not be construed to limit the scope of the disclosure. Various modifications and changes may be made to the principles described herein without following the example embodiments and applications illustrated and described herein, and without departing from the spirit and scope of the disclosure.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described. For example, it is to be understood that the present disclosure contemplates that, to the extent possible, one or more features of any embodiment can be combined with one or more features of any other embodiment.

I claim:

1. A system for peer review, comprising:

a processor;

a storage configured to receive a request from a medical provider, said request comprising identified medical data that is uniquely associated with a patient and that is uniquely associated with said medical provider;

an anonymizer configured to receive said identified medical data from said storage, generate anonymized medical data by removing any association with said patient and any association with said medical provider from said identified medical data, resulting in said anonymized medical data, and provide said anonymized medical data to a plurality of reviewers;

a score generator configured to:

determine whether a current score from previous assessments of said plurality of reviewers is below a pre-defined threshold score;

in response to said current score being below said pre-defined threshold score, receive, from said plurality of reviewers, a plurality of assessments corresponding to said anonymized medical data, update said current score based on the plurality of assessments, and determine whether criteria to finalize said current score has been met;

in response to said current score not being below said pre-defined threshold score or said criteria having been met, provide said plurality of assessments of said anonymized medical data as input to a model trained on a plurality of previous treatments and a corresponding plurality of previous scores associated with said plurality of previous treatments;

execute said model using said input;

generate a score from said executed model, wherein said score represents a quality of a treatment of said patient by said medical provider; and determine a region of a plurality of regions of a numerical scale that said score is within;

a report generator configured to receive said score from said score generator and display a report comprising said score and said determined region to said medical provider; and a non-transitory computer readable medium storing a set of instructions, which when executed by said processor, configure said anonymizer, said score generator, and said report generator.

2. The system of claim 1, wherein said anonymizer is further configured to normalize said identified medical data, wherein normalizing said identified medical data comprises transforming said identified medical data to a particular format.

3. The system of claim 1, wherein said report generator is further configured to receive said plurality of assessments, and said report further comprises said plurality of assessments.

4. The system of claim 1, wherein said anonymizer is an anonymizer service.

5. The system of claim 1, wherein said storage is a first storage, said system further comprising:

a second storage adapted for storing identified medical data; and a parser configured to:

extract said identified medical data from said first storage;

transform said identified medical data to a particular format; and store said transformed identified medical data in said second storage, wherein said anonymizer is further configured to receive said transformed identified medical data from said second storage, and said set of instructions, when executed by said processor, configure said parser.

6. The system of claim 1, wherein said storage is a first storage, wherein said system further comprises a second storage adapted for storing said anonymized medical data, wherein said anonymizer is further configured to store said anonymized medical data in said second storage, and wherein said second storage is configured to provide said anonymized medical data to said plurality of reviewers.

7. The system of claim 1, wherein said report is an anonymized report that does not identify any of said plurality of reviewers.

8. The system of claim 1, wherein said identified medical data further comprises at least one of a date, a case number, and an account identifier.

9. The system of claim 8, wherein said anonymizer is further configured to generate said anonymized medical data by at least one of replacing said account identifier with an anonymized account identifier and replacing said case number with an anonymized case number.

10. The system of claim 1, wherein said identified medical data comprises a description of said treatment and said plurality of assessments comprise a plurality of assessments of said quality of said treatment based on said description.

11. The system of claim 10, wherein said description of said treatment comprises a description of a medical condition of said patient, said treatment is for said medical condition, and said report further comprises a comparison between said treatment and an optimal treatment for said medical condition.

12. The system of claim 1, further comprising a validator configured to receive said request from said medical provider, validate said request to determine whether said identified medical data is complete, and, based on a determination that said identified medical data is complete, provide said request to said storage, wherein said storage is further configured to receive said request from said validator, and said set of instructions, when executed by said processor, configure said validator.

13. The system of claim 12, wherein said validator is further configured to receive said anonymized medical data from said anonymizer, validate said anonymized medical data to determine whether said anonymized medical data is complete, and, based on a determination that said anonymized medical data is complete, provide said anonymized medical data to said plurality of reviewers, wherein said anonymizer is further configured to provide said anonymized medical data to said validator.

14. The system of claim 1, wherein said identified medical data is uniquely associated with said patient using a patient identifier, and said anonymizer is further configured to remove all occurrences of said patient identifier from said identified medical data.

15. The system of claim 14, wherein removing all occurrences of said patient identifier comprises replacing said patient identifier with an anonymized patient identifier.

16. The system of claim 1, wherein said medical provider is a person that is capable of providing treatment to said patient, said identified medical data is uniquely associated with said medical provider using a provider identifier, and said anonymizer is further configured to remove all occurrences of said provider identifier from said identified medical data.

17. The system of claim 16, wherein removing all occurrences of said provider identifier comprises replacing said provider identifier with an anonymized provider identifier.

18. The system of claim 1, wherein said identified medical data is uniquely associated with a medical organization, and said anonymizer is further configured to remove any association with said medical organization.

19. The system of claim 18, wherein said identified medical data is uniquely associated with said medical organization using an organization identifier, and said anonymizer is further configured to remove all occurrences of said organization identifier from said identified medical data.

20. The system of claim 1, wherein said score generator is further configured to combine said plurality of assessments into an aggregate assessment and generate said score based on said aggregate assessment.

21. The system of claim 1, wherein said criteria comprises one or more of:

a predefined maximum number of reviewers; and a number of iterations for comparing said current score to said pre-defined threshold score.

22. The system of claim 21, wherein said plurality of reviewers is a first plurality of reviewers, said score is a first score, and said plurality of assessments is a first plurality of assessments, and said score generator is further configured to:

define a threshold score, wherein a score above said threshold score indicates said quality of said treatment is a valid treatment and a score below said threshold score indicates said quality of said treatment is an invalid treatment;

make a determination that said first score is below said threshold score;

based on said determination, direct said anonymizer to provide said anonymized medical data to a second plurality of reviewers;

receive, from said second plurality of reviewers, a second plurality of assessments of said anonymized medical data; and update said first score based on said first plurality of assessments and said second plurality of assessments.

23. The system of claim 22, wherein said score generator is further configured to generate a plurality of initial scores, each corresponding to one of said plurality of assessments, and combine said plurality of initial scores into said score, wherein said plurality of initial scores is a first plurality of initial scores, and wherein said score generator is further configured to:

generate a second plurality of initial scores, each corresponding to one of said second plurality of assessments;

combine said first plurality of initial scores and said second plurality of initial scores into a second score; and replace said first score with said second score.

24. The system of claim 1, wherein said score generator is further configured to:

receive training data, said training data comprising said generated score and a plurality of descriptions of said plurality of previous treatments of a plurality of previous patients, and further comprising a corresponding plurality of previous scores, wherein said corresponding plurality of previous scores represent a quality of said plurality of previous treatments;

re-train said model using said training data, resulting in a re-trained model; and provide said plurality of assessments to said re-trained model to generate a new score.

* * * * *